(12) United States Patent
Tessonnier et al.

(10) Patent No.: US 10,465,043 B2
(45) Date of Patent: Nov. 5, 2019

(54) ELECTROCHEMICAL ISOMERIZATION OF MUCONIC ACID

(71) Applicant: Iowa State University Research Foundation, Inc., Ames, IA (US)

(72) Inventors: Jean-Philippe Tessonnier, Ames, IA (US); John Edward Matthiesen, Ames, IA (US); Toni Pfennig, Ames, IA (US); Brent Shanks, Ames, IA (US); Jack M. Carraher, Ames, IA (US)

(73) Assignee: Iowa State University Research Foundation, Ames, IA (US)

( * ) Notice: Subject to any disclaimer, the term of this patent is extended or adjusted under 35 U.S.C. 154(b) by 202 days.

(21) Appl. No.: 15/348,122

(22) Filed: Nov. 10, 2016

(65) Prior Publication Data

US 2017/0129995 A1 May 11, 2017

Related U.S. Application Data

(60) Provisional application No. 62/253,456, filed on Nov. 10, 2015.

(51) Int. Cl.
*C07C 51/00* (2006.01)
*C25B 3/00* (2006.01)
(Continued)

(52) U.S. Cl.
CPC ............ *C08G 63/78* (2013.01); *B01J 19/088* (2013.01); *C07C 51/347* (2013.01); *C07C 51/353* (2013.01); *C07C 51/377* (2013.01); *C08G 63/183* (2013.01); *B01J 2219/0809* (2013.01); *B01J 2219/0877* (2013.01); *C07B 2200/09* (2013.01); *C07C 2601/14* (2017.05)

(58) Field of Classification Search
CPC .......... C07C 51/353; C07C 55/00; C25B 3/04
USPC .......................................... 562/591; 205/440
See application file for complete search history.

(56) References Cited

U.S. PATENT DOCUMENTS

| 3,032,489 A | 5/1962 | Loveland |
| 4,001,187 A * | 1/1977 | Itabashi ............... C08G 63/183 528/274 |

(Continued)

FOREIGN PATENT DOCUMENTS

| JP | 03285090 A * | 12/1991 | ............... C25B 3/04 |
| JP | 03285090 A | 12/1991 | |
| WO | WO-2016077361 A1 | 5/2016 | |

OTHER PUBLICATIONS

"U.S. Appl. No. 62/077,697, Preliminary Amendment filed Feb. 25, 2015", 3 pgs.

(Continued)

*Primary Examiner* — Edna Wong
(74) *Attorney, Agent, or Firm* — Schwegman Lundberg & Woessner, P.A.

(57) ABSTRACT

Various embodiments disclosed relate to electrochemical isomerization of muconic acid. In various embodiments, the present invention provides a method to prepare trans,trans-muconic acid. The method can include passing current through a catalytic cathode in a reactor including an aqueous acidic solution including cis,trans-muconic acid, a supporting electrolyte, and an anode, so as to isomerize the cis,trans-muconic acid to yield a product including trans trans-muconic acid.

20 Claims, 18 Drawing Sheets

(51) Int. Cl.
| | |
|---|---|
| C08G 63/78 | (2006.01) |
| C07C 51/353 | (2006.01) |
| C07C 51/347 | (2006.01) |
| C07C 51/377 | (2006.01) |
| B01J 19/08 | (2006.01) |
| C08G 63/183 | (2006.01) |

(56) References Cited

U.S. PATENT DOCUMENTS

| | | | |
|---|---|---|---|
| 5,225,581 A | 7/1993 | Pintauro | |
| 2010/0314243 A1* | 12/2010 | Frost | C07C 51/353 204/157.15 |
| 2011/0124911 A1 | 5/2011 | Burk et al. | |
| 2015/0096897 A1* | 4/2015 | Hashiba | C25B 11/0494 205/450 |
| 2017/0342575 A1 | 11/2017 | Tessonnier et al. | |

OTHER PUBLICATIONS

"International Application Serial No. PCT/US15/59974, Invitation to Pay Add'l Fees and Partial Search Rpt dated Jan. 26, 2016".
"International Application Serial No. PCT/US2015/059974, International Search Report dated Apr. 6, 2016", 8 pgs.
"International Application Serial No. PCT/US2015/059974, Written Opinion dated Apr. 6, 2016", 10 pgs.
"U.S. Appl. No. 15/524,888, Preliminary Amendment Filed May 5, 2017", 7 pgs.
"International Application Serial No. PCT/US2015/059974, International Preliminary Report on Patentability dated May 26, 2017", 12 pgs.
Ogumi, Z, "Application of the spe method to organic electrochemistry-II. Electrochemical hydrogenation of olefinic double bonds", Electrochimica Acta, Elsevier Science Publishers, Barking, GB, vol. 26, No. 12, (Dec. 1, 1981), 1779-1782.
Chiba, Toshiro, et al., "Electrocatrocatalyic Reduction Using Raney Nickel", Bull. Chem. Soc. Jpn., 56, (1983), 719-723.
Curran, K. A., et al., "Metabolic engineering of muconic acid production in *Saccharomyces cerevisiae* ", Metabolic Engineering, 15, (Jan. 2013), 55-66.
Greeley, J., et al., "Computational high-throughput screening of electrocatalytic materials for hydrogen evolution", Nat. Mater., 5(11), (2006), 909-913.
Kirilyus, I. V., et al., "Electrocatalytic Reduction of Pyridine at Raney Nickel", Translated from Elektrokhimiya, 15(10), pp. 1545-1546, Oct. 1979, (1979), 2 pgs.
Miller, L. L., et al., "Electrocatalytic hydrogenation of aromatic compounds", J. Org. Chem., 43(10), (1978), 2059-2061.
Park, K., et al., "Flow Reactor Studies of the Paired Electro-Oxidation and Electroreduction of Glucose", J. Electrochem. Soc., 132(8), (1985), 1850-1855.
Trasatti, S., "Work function, electronegativity, and electrochemical behaviour of metals: III. Electrolytic hydrogen evolution in acid solutions", Journal of Electroanalytical Chemistry and Interfacial Electrochemistry, 39(1), (1972), 163-184.
Weber, C., et al., "Biosynthesis of cis,cis-Muconic Acid and Its Aromatic Precursors, Catechol and Protocatechuic Acid, from Renewable Feedstocks by *Saccharomyces cerevisiae*", Appl. Env. Microbiol., 78(23), (2012), 8421-8430.

* cited by examiner

ELECTROCHEMICAL ISOMERIZATION OF MUCONIC ACID

CROSS-REFERENCE TO RELATED APPLICATION

This application claims the benefit of priority to U.S. Provisional Patent Application Ser. No. 62/253,456 filed Nov. 10, 2015, the disclosure of which is incorporated herein in its entirety by reference.

STATEMENT OF GOVERNMENT SUPPORT

This invention was made with Government support under EEC0813570 awarded by the National Science Foundation. The U.S. Government has certain rights in this invention.

BACKGROUND

As shown in Scheme 1, muconic acid ("MA") is an unsaturated dicarboxylic acid, hexe-2,4-dienedoic acid, which can exist in three isomeric forms.

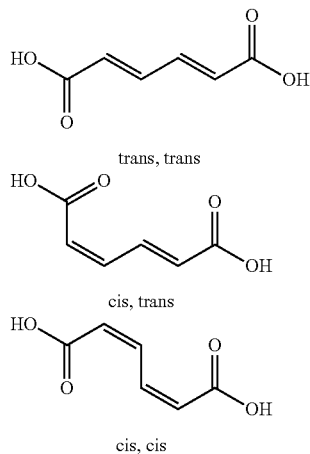

Scheme 1.

Techniques that isomerize cis,trans-muconic acid to trans,trans-muconic acid typically involve chemicals such as iodine and organic solvents, and require additional steps of separation and purification after isomerization to isolate the desired isomer.

SUMMARY OF THE INVENTION

In various embodiments, the present invention provides an electrocatalytic method to prepare trans,trans-muconic acid. The method includes passing current through a catalytic cathode in a reactor including an aqueous acidic solution including cis,trans-muconic acid, a supporting electrolyte, and an anode, so as to isomerize the cis,trans-muconic acid to yield a product including trans,trans-muconic acid.

In various embodiments, the present invention provides an electrocatalytic method to prepare trans,trans-muconic acid from cis,trans-muconic acid. The method includes passing current through a catalytic cathode including Pb, wherein the catalytic cathode is in a reactor including an aqueous acidic solution including cis,trans-muconic acid, a supporting electrolyte, and an anode, so as to isomerize the muconic acid so as to yield a product including trans,trans-muconic acid.

In various embodiments, the present invention provides an electrocatalytic method to prepare terephthalic acid from cis,trans-muconic acid. The method includes passing current through a catalytic cathode in a reactor including an aqueous acidic solution including cis,trans-muconic acid, a supporting electrolyte, and an anode, so as to isomerize the cis,trans-muconic acid to yield a product including trans,trans-muconic acid. The method includes reacting the trans,trans-muconic acid with ethylene to form a Diels-Alder adduct. The method also includes aromatizing the Diels-Aider adduct, to provide terephthalic acid.

In various embodiments, the method of isomerizing muconic acid can have advantages over other methods of forming trans,trans-muconic acid, at least some of which are unexpected. For example, in some embodiments, the present method can be performed without iodine or other organic solvents, or can be performed using less organic solvents or other toxic materials than other methods of forming trans,trans-muconic acid. In various embodiments, the present method of isomerizing muconic acid to form trans,trans-muconic acid can be performed in an aqueous solution using a solid catalyst (e.g., a heterogeneous reaction).

In some embodiments, the present method can be a more efficient and more effective way to generate trans,trans-muconic acid and products derivable therefrom than other methods. In some embodiments, the present method can have a higher selectivity of trans,trans-muconic acid from cis,trans-muconic acid, from cis,cis-muconic acid, or a combination thereof, than other methods. In some embodiments, the present method can have a higher percent conversion of starting materials than other methods, such as a higher conversion of cis,trans-muconic acid, of cis,cis-muconic acid, or of a combination thereof.

In various embodiments, the present method can provide an efficient way to form the Diels-Alder diene trans,trans-muconic acid. In various embodiments, the produced trans,trans-muconic acid can be reacted with ethylene in a Diels-Alder reaction to form a Diels-Alder adduct which can then be aromatized to provide terephthalic acid. In various embodiments, the present method can provide a more economical, more efficient, and more environmentally-friendly route to terephthalic acid than other methods, including as compared to other methods that start with muconic acid. In various embodiments, the terephthalic acid can be polymerized to form polyethylene terephthalate (PET), providing a more economical, more efficient, and more environmentally-friendly route to PET than other methods.

BRIEF DESCRIPTION OF THE FIGURES

The drawings illustrate generally, by way of example, but not by way of limitation, various embodiments discussed in the present document.

DETAILED DESCRIPTION OF THE INVENTION

Figure 1:
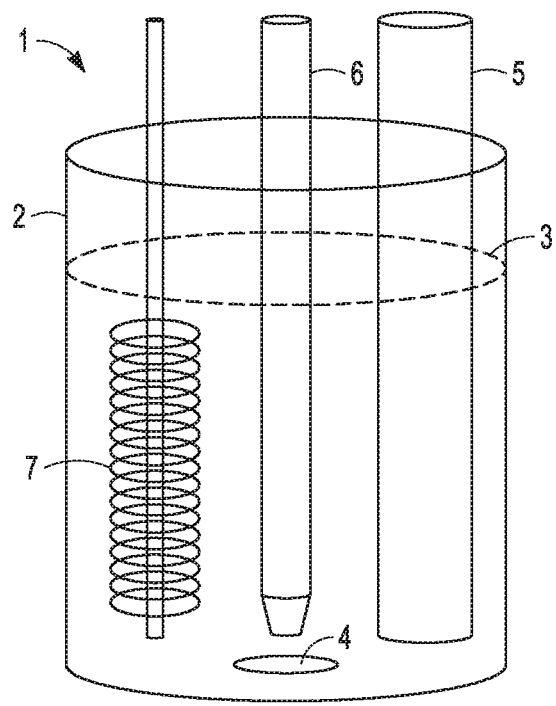
FIG. 1 is a schematic drawing of a three-electrode electrochemical cell, according to various embodiments.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. A comma can be used as a delimiter or digit group separator to the left or right of a decimal mark; for example, "0.000,1" is equivalent to "0.0001." All publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%.

The term "organic group" as used herein refers to any carbon-containing functional group. Examples can include an oxygen-containing group such as an alkoxy group, aryloxy group, aralkyloxy group, oxo(carbonyl) group; a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_2$, OCF$_3$, R, C(O), methylenedioxy, ethylenedioxy, N(R)$_2$, SR, SOR, SO$_2$R, SO$_1$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, C(=NOR)R, and substituted or unsubstituted (C$_1$-C$_{100}$)hydrocarbyl, wherein R can be hydrogen (in examples that include other carbon atoms) or a carbon-based moiety, and wherein the carbon-based moiety can be substituted or unsubstituted.

The term "substituted" as used herein in conjunction with a molecule or an organic group as defined herein refers to the state in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enmities; and other heteroatoms in various other groups. Non-limiting examples of substituents that can be bonded to a substituted carbon (or other) atom include. F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein R can be hydrogen or a carbon-based moiety; for example, R can be hydrogen, (C$_1$-C$_{100}$)hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The term "acyl" as used herein refers to a group containing a carbonyl moiety wherein the group is bonded via the carbonyl carbon atom. The carbonyl carbon atom is bonded to a hydrogen forming a "formyl" group or is bonded to another carbon atom, which can be part of an alkyl, aryl, aralkyl cycloalkyl, cycloalkylalkyl, heterocyclyl, heterocylylalkyl, heteroaryl, heteroarylalkyl group or the like. An acyl group can include 0 to about 12, 0 to about 20, or 0 to about 40 additional carbon atoms bonded to the carbonyl group. An acyl group can include double or triple bonds within the meaning herein. An acryloyl group is an example of an acyl group. An acyl group can also include heteroatoms within the meaning herein. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" as used herein refers to cyclic aromatic hydrocarbon groups that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, a phenyl group substituted at any one or more of 2-, 3-, 4-, 5-, or 6-positions of the phenyl ring, or a naphthyl group substituted at any one or more of 2- to 8-positions thereof.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

The term "hydrocarbon" or "hydrocarbyl" as used herein refers to a molecule or functional group, respectively, that includes carbon and hydrogen atoms. The term can also refer to a molecule or functional group that normally includes both carbon and hydrogen atoms but wherein all the hydrogen atoms are substituted with other functional groups.

As used herein, the term "hydrocarbyl" refers to a functional group derived from a straight chain, branched, or cyclic hydrocarbon, and can be alkyl, alkenyl, alkynyl, aryl, cycloalkyl, acyl, or any combination thereof. Hydrocarbyl groups can be shown as (C$_a$-C$_b$)hydrocarbyl, wherein a and b are integers and mean having any of a to b number of carbon atoms. For example, (C$_1$-C$_4$)hydrocarbyl means the hydrocarbyl group can be methyl (C$_1$), ethyl (C$_2$), propyl (C$_3$), or butyl (C$_4$), and (C$_0$-C$_b$)hydrocarbyl means in certain embodiments there is no hydrocarbyl group.

The term "solvent" as used herein refers to a liquid that can dissolve a solid, liquid, or gas. Non-limiting examples of solvents are silicones, organic compounds, water, alcohols, ionic liquids, and supercritical fluids.

The term "room temperature" as used herein refers to a temperature of about 15° C. to 28° C.

In various embodiments, salts having a positively charged counterion can include any suitable positively charged counterion. For example, the counterion can be ammonium (NH$_4^+$), or an alkali metal such as sodium (Na$^+$), potassium (K$^+$), or lithium (Li$^+$). In some embodiments, the counterion can have a positive charge greater than +1, which can in some embodiments complex to multiple ionized groups, such as Zn$^{2+}$, Al$^{3+}$, or alkaline earth metals such as Ca$^{2+}$ or Mg$^{2+}$.

In various embodiments, salts having a negatively charged counterion can include any suitable negatively charged counterion. For example, the counterion can be a halide, such as fluoride, chloride, iodide, or bromide. In other examples, the counterion can be nitrate, hydrogen sulfate, dihydrogen phosphate, bicarbonate, nitrite, perchlorate, iodate, chlorate, bromate, chlorite, hypochlorite, hypobromite, cyanide, amide, cyanate, hydroxide, permanganate. The counterion can be a conjugate base of any carboxylic acid, such as acetate or formate. In some embodiments, a counterion can have a negative charge greater than −1, which can in some embodiments complex to multiple ionized groups, such as oxide, sulfide, nitride, arsenate, phosphate, arsenite, hydrogen phosphate, sulfate, thiosulfate, sulfite, carbonate, chromate, dichromate, peroxide, or oxalate.

Method of Preparing Trans,Trans-Muconic Acid.

In various embodiments, the present invention provides an electrocatalytic method to prepare trans,trans-muconic acid. The method can include passing current through a catalytic cathode in a reactor including an aqueous acidic solution including cis,trans-muconic acid. The reactor also includes a supporting electrolyte and an anode. The passing of the current through the cathode is effective to isomerize the cis,trans-muconic acid to yield a product including trans,trans-muconic acid.

In some embodiments, hydrogen is generated on the catalyst surface by the electrochemical reduction of protons or water in the electrolyte. In other embodiments, no hydrogen is generated on the catalyst surface during the isomerization to form the trans,trans-muconic acid. The isomerization to form the trans,trans-muconic acid can occur with zero electron transfer.

High operating temperatures and pressures are not required. The isomerization can be carried out at any suitable temperature and pressure. The isomerization can be conducted under ambient conditions of temperature and pressure, such as about 20° to about 30° C. and at about 1 atm, for a time sufficient to complete the isomerization, e.g., for about 1 minute to about 24 hours, about 0.5 h to about 24 h, about 1 h to about 6 h, or about 1 h or less, or less than, equal to, or greater than about 2 h, 3, 4, 5, 6, 7, 8, 9, 10, 11, 12, 13, 14, 15, 16, 17, 18, 19, 20, 21, 22, 23, or about 24 h or more.

The isomerization can be carried out in an acidified aqueous medium, such as water or even a yeast fermentation broth (e.g., medium) employed to prepare the muconic acid. The medium can be acidified with, e.g., an inorganic or organic acid, such as formic acid, sulfuric acid, a salt thereof (e.g., that provides an electrolyte), or a combination thereof. The acidified aqueous solution can include a salt of an organic acid, a salt of a mineral acid, or a combination thereof. The aqueous acidic solution can include a sulfate salt, a formate salt, or a combination thereof. The aqueous acidic solution can include potassium sulfate, sodium sulfate, potassium formate, sodium formate, or a combination thereof.

The acidified aqueous medium can be an electrolyte. The medium can be contained in a reactor that includes an anode (e.g., the counter electrode), a cathode (e.g., the working electrode), and a reference electrode (e.g., an Ag/AgCl electrode or a reversible hydrogen electrode). The reactor can be any suitable reactor having any suitable shape, such that the method can be carried out as described herein. The reactor can be a batch reactor. The reactor can be a continuous flow reactor.

The muconic acid can be produced in any suitable way. In some embodiments, the muconic acid is commercially obtained. In some embodiments, the muconic acid is produced from petroleum materials. In some embodiments, the muconic acid is produced from a microorganism or an enzyme, such as any suitable microorganism or enzyme. The muconic acid can be produced by yeast or bacteria, such as any suitable yeast or bacteria. The microorganism (e.g., yeast or bacteria) or enzyme can use any suitable organic material to generate the muconic acid, such as a carbohydrate (e.g., glucose), or such as an aromatic material (e.g., lignin). In some embodiments, the muconic acid is generated by yeast in a fermentation broth. The aqueous solution can include an acidic fermentation broth including the cis,trans-muconic acid.

The fermentation broth can be any suitable fermentation broth. The fermentation broth can include glucose and support the conversion of glucose into inuconic acid by yeast, such as any suitable type of yeast that can perform the conversion. The fermentation broth can include yeast nitrogen base. The yeast nitrogen base can be substantially free of amino acids, ammonium sulfate, or a combination thereof. The fermentation broth can include complete supplement mixture (CSM) uracil-dropout amino acid mix. The method can include at least partially simultaneously fermenting the broth to form cis,trans-muconic acid from the yeast (e.g., either directly or via production of cis,cis-muconic acid followed by isomerization to the cis,trans-muconic acid) and isomerizing cis,trans-muconic acid in the broth.

The cathode can include any suitable material, such that the method can be carried out as described herein. The cathode used in the reaction can utilize both high and low hydrogen overvoltage catalytic metals, e.g., lead or another metal such as platinum, vanadium, chromium, manganese, iron, cobalt, zinc, aluminum, titanium, zirconium, niobium, molybdenum, ruthenium, palladium, cadmium, indium, samarium, antimony, hafnium, tantalum, rhenium, iridium, gold, bismuth, tungsten, nickel, copper, silver, alloys thereof, or combinations thereof. The cathode can include, or can be, one or more transition metals. The cathode can include, or can be, one or more platinum group metals. The cathode can include, or can be, at least one of Cu, Fe, Ni, Pd, Pt, Pd/C, Pb, Sn, Ti, Zn, or a combination thereof. The cathode can include, or can be, lead. The cathode can include, or can be, platinum.

The material used for the anode is not critical. Suitable anodes can include graphite, platinum, platinum-coated titanium, ruthenium oxide titanium oxide-coated titanium, or combinations thereof. The anodic reaction can be the oxidation of water to produce oxygen gas.

The electric potential applied to the cathode with a respect to a reference electrode (e.g., an Ag/AgCl reference electrode or a reversible hydrogen electrode in the electrolyte solution with the anode and cathode) can be adjustable and can be maintained at about −0.1 V to about −5 V, about −0.3 V to about −3.0 V, about −0.5 V to about −3.0 V, about −0.5 V to about −2.0 V, about −0.5 V to about −1.5 V, about −0.8 V to −1.8 V, or about −0.1 or more, or less than, equal to, or greater than about −0.2, −0.3, −0.4, −0.5, −0.6, −0.7, −0.8, −0.9, −1, −1.1, −1.2, −1.3, −1.4, −1.5, −1.6, −1.7, −1.8, −1.9, −2, −2.1, −2.2, −2.4, −2.6, −2.8, −3, −3.2, −3.4, −3.6, −3.8, −4, −4.2, −4.4, −4.6, −4.8, or about −5 V.

The muconic acid starting material can be any suitable muconic acid including cis, trans-muconic acid. The muconic acid can further include be cis,cis-muconic; acid, trans,trans-muconic acid, or a combination thereof. In various embodiments, the muconic acid starting material is about 0 mol % to about 99.999 mol % cis,cis-muconic; acid, or about 0 mol % (e.g., the muconic acid starting material can be substantially free of cis,cis-muconic acid), or about 0.001 mol % or less, or less than, equal to, or more than about 0.01 mol %, 0.1, 1, 2, 3, 4, 5, 6, 8, 10, 12, 14, 16, 18, 20, 25, 30, 35, 40, 45, 50, 55, 60, 65, 70, 75, 80, 82, 84, 86, 88, 90, 91, 92, 93, 94, 95, 96, 97, 98, 99, 99.9, 99.99, or about 99.999 mol % or more. In various embodiments, the muconic acid starting material is about 0.001 mol % to about 100 mol % cis,trans-muconic acid, or about 0.001 mol % or less, or less than, equal to, or more than about 0.01 mol %, 0.1, 1, 2, 3, 4, 5, 6, 8, 10, 12, 14, 16, 18, 20, 25, 30, 35, 40, 45, 50, 55, 60, 65, 70, 75, 80, 82, 84, 86, 88, 90, 91, 92, 93, 94, 95, 96, 97, 98, 99, 99.9, 99.99, or about 99.999 mol % or more, or about 100 mol %. In various embodiments, the muconic acid starting material is about 0 mol % to about 100 mol % trans,trans-muconic acid, or about 0 mol % (e.g., the muconic acid starting material can be substantially free of trans,trans-muconic acid), or about 0.001 mol % or less, or less than, equal to, or more than about 0.01 mol %, 0.1, 1, 2, 3.4, 5, 6, 8, 10, 12, 14, 16, 18, 20, 25, 30, 35, 40, 45, 50, 55, 60, 65, 70, 75, 80, 82, 84, 86, 88, 90, 91, 92, 93, 94, 95, 96, 97, 98, 99, 99.9, 99.99, or about 99.999 mol % or more, or about 100 mol %. In embodiments wherein the muconic acid starting material includes trans,trans-muconic acid, the product has a higher concentration of trans,trans-muconic acid than the muconic acid starting material.

In some embodiments, a muconic acid starting material can be used that is substantially free of cis,trans-muconic acid (e.g., about 0 mol % or wt %) but that includes cis,cis-muconic acid. In such embodiments, the cis,cis-muconic acid can be isomerized to cis,trans-muconic acid (e.g., via the same electrocatalytic method for isomerization of cis,trans-muconic acid described here), which can then be isomerized to the trans,trans-muconic acid. In such embodiments, the isomerization of the cis,cis-muconic acid to the cis,trans-muconic acid can occur prior to the beginning of embodiments of the present method, or can be part of embodiments of the present method.

The product of the electrocatalytic isomerization of the cis,trans-muconic acid includes trans,trans-muconic acid in any suitable wt % or mol %. For example, the product can be about 0 wt % to about 100 wt. % trans,trans-muconic acid, or about 0 wt %, or about 0.001 wt % or less, or less than, equal to, or more than about 0.01 wt %, 0.1, 1, 2, 3, 4, 5, 6, 8, 10, 12, 14, 16, 18, 20, 25, 30, 35, 40, 45, 50, 55, 60, 65, 70, 75, 80, 82, 84, 86, 88, 90, 91, 92, 93, 94, 95, 96, 97, 98, 99, 99.9, 99.99, or about 99.999 wt % or more, or about 100 wt %. For example, the product can be about 0 mol % to about 100 mol % trans,trans-muconic acid, or about 0 mol %, or about 0.001 mol % or less, or less than, equal to, or more than about 0.01 mol %, 0.1, 1, 2, 3, 4, 5, 6, 8, 10, 12, 14, 16, 18, 20, 25, 30, 35, 40, 45, 50, 55, 60, 65, 70, 75, 80, 82, 84, 86, 88, 90, 91, 92, 93, 94, 95, 96, 97, 98, 99, 99.9, 99.99, or about 99.999 mol % or more, or about 100 mol %.

The electrocatalytic isomerization of the cis,trans-muconic acid can have any suitable selectivity for trans,trans-muconic acid, such as about 0% to about 100% (e.g., 0 mol % to about 100 mol % of the cis,trans-muconic acid isomerized or otherwise reacted can be trans,trans-muconic acid), about 0.01% to about 100%, about 25% to about 60%, or about 0%, or about 0.001% or less, or less than, equal to, or greater than about 0.01%, 0.1, 1, 2, 3, 4, 5, 6, 7, 8, 9, 10, 12, 14, 16, 18, 20, 25, 30, 35, 40, 45, 50, 55, 60, 65, 70, 75, 80, 82, 84, 86, 88, 90, 91, 92, 93, 94, 95, 96, 97, 98, 99, 99.9, 99.99, or about 99.999% or more, or about 100%.

The cis,trans-muconic acid can be converted with any suitable percent conversion, such as about 40% to about 1.00%, about 35% to about 80%, about 80% to about 100%, or about 90% to about 100%, or about 95% to about 100%, or about 40% or less, or less than, equal to, or greater than about 45, 50, 55, 60, 65, 70, 75, 80, 81%, 82, 83, 84, 85, 86, 87, 88, 89, 90, 91, 92, 93, 94, 95, 96, 97, 98, 99, 99.9, 99.99, or about 99.999% or more, or about 100%.

Method of Preparing Terephthalic Acid.

In various embodiments, the present invention provides a method of preparing substituted or unsubstituted terephthalic acid. Trans,trans-muconic acid is a suitable dienophile for a Diels-Alder reaction. In various embodiments, the method includes reacting the trans,trans-muconic acid with a Diels-Alder dienophile to form a Diels-Alder adduct.

The Diels-Alder dienophile can be any suitable dienophile. The Diels-Alder dienophile can be a substituted or unsubstituted ethylene, wherein the Diels-Alder adduct is a tetrahydrogenated substituted or unsubstituted terephthalic acid.

The method can further include aromatizing the Diels-Alder adduct (e.g., dehydrogenating, such as to remove 4 hydrogen atoms from the tetahydrogenated ring of the Diels-Alder adduct), to provide an aromatic compound. For example, the dienophile can be a substituted or unsubstituted ethylene, and the aromatized Diels-Alder adduct can be a substituted or unsubstituted terephthalic acid. For example, the dienophile can be an unsubstituted ethylene, and the aromatized Diels-Alder adduct can be terephthalic, acid. The aromatization can be performed using any suitable dehydrogenation reagents, such as using Pd/C.

In some embodiments, the Diels-Alder reaction can be performed at elevated temperatures, in γ-vaierolactone (GVL), or in dioxane, the dienophile can be a substituted or unsubstituted ethylene, and the Diels-Alder adduct can be a substituted or unsubstituted cyclohex-1-ene-1,4-dicarboxylic acid and substantially no substituted or unsubstituted cyclohex-2-ene-1,4-dicarboxylic acid is formed.

The method can include esterifying the trans,trans-muconic acid (e.g., $(C_{1-10})$alkyl ester, such as methyl or ethyl, or using ethylene glycol, propylene glycol, polyethylene glycol, or polypropylene glycol) and reacting the esterification product with a Diels-Alder dienophile to form a Diels-Alder adduct. Such esterification can prevent isomerization of the Diels-Alder product. The dienophile can be a substituted or unsubstituted ethylene, and the Diels-Alder adduct is a substituted or unsubstituted cyclohex-2-ene-1,4-dicarboxylic acid with substantially no formation of substituted or unsubstituted cyclohex-1-ene-1,4-dicarboxylic acid.

Method of Preparing Polyethylene Terephthalate.

In various embodiments, the present invention includes polymerizing a Diels-Alder adduct formed from the trans,trans-muconic acid (e.g., an unaromatized product). The Diels-Alder adduct can be polymerized with any suitable material, such as ethylene glycol, to provide a polymer. In some embodiments, the resulting polymer can be subsequently vulcanized.

In various embodiments, the present invention provides a method of preparing polyethylene terephthalate. The method can include forming the trans,trans-muconic acid, reacting the trans,trans-muconic acid with substituted (e.g., with electron-withdrawing groups) or unsubstituted ethylene to form a Diels-Alder adduct, aromatizing the Diels-Alder adduct to give a substituted or unsubstituted terephthalic acid, and polymerizing the substituted or unsubstituted terephthalic acid with substituted or unsubstituted ethylene glycol to give a substituted or unsubstituted polyethylene terephthalate. In some embodiments, the dienophile is unsubstituted ethylene, and the ethylene glycol is unsubstituted, such that the aromatized product is unsubstituted terephthalic acid, and the polymer is unsubstituted polyethylene terephthalate.

In various embodiments, the method includes performing the electrochemical isomerization under pressure of ethylene to produce the Diels-Alder adduct under low temperatures and in fermentation broth.

EXAMPLES

Various embodiments of the present invention can be better understood by reference to the following Examples which are offered by way of illustration. The present invention is not limited to the Examples given herein.

Part 1

Electrocatalytic hydrogenation is used to hydrogenate cis,trans-MA (ctMA) to two monomers, adipic acid, and trans-3-hexenedioic acid, used for the production of nylon, nylon derivatives, and polyester ethers). The electrocatalytic hydrogenation considers a wide range of early, late, and post transition metals (Cu, Fe, Ni, Pb, Pd/C, Sn, Ti, and Zn) with low and high hydrogen overpotentials; this selection possesses varying degrees of metal hydrogen binding strengths. The binding strength was determined to be an important factor for the conversion rate, faradaic efficiency, and selectivity of the hydrogenation. Selectivities are also discussed in relation to thermodynamic data, which suggests the possibility to tune the kinetics of the reaction to allow for the variable production of multiple monomers. Ph and Pd/C were identified as potential catalysts for the production of trans-3-hexenedioic acid and adipic acid, respectively. trans-3-Hexenedioic acid (t3HDA) is a bio-based chemical that has been rarely observed and only in low yields during the semi-hydrogenation of MA under pressurized $H_2$. Further analysis of Ph and Pd/C revealed turnover frequencies of 5.6 $s^{-1}$ and 0.1 $s^{-1}$, respectively.

Example 1-1

(1-1)(A). Materials and Methods.
Electrocatalysis.
The electrochemical studies were conducted her a conventional single compartment three-electrode glass cell (1) depicted in FIG. 1. The container (2) was about 2.54 cm in diameter and about 3.8 cm high. The electrolyte level (3) shown is approximate. Current was passed through an aqueous reaction medium (3) including 1% formic acid in water (electrolyte) and varying concentrations of muconic acid. An Ag/AgCl reference electrode in 3 M NaCl ($E^0$=+ 0.194 V vs. NHE) (6) and platinum counter electrode (7) were purchased from BioLogic Science Instruments. A 10 $cm^2$ Pb rod (Rotometals, 99.9% purity) working electrode was used (5). Controlled voltage was applied using a Biologic VSP-300 potentiostat from BioLogic Science instruments (not shown). The electrolyte was agitated via magnetic stirring using stir bar (4). The solutions were magnetically stirred at 700 rpm with a PTFE flea stir bar.

All potentials in this Part are in reference to the reversible hydrogen electrode (RHE). Initial experiments to determine reaction schemes and product decomposition were performed with 11 ml solution of muconic acid dissolved in 0.01 M sulfuric acid electrolyte ($H_2SO_4$). During chronoamperometry experiments, 0.5 ml aliquots of the reaction medium were withdrawn periodically.

Catalysts screenings were conducted with a 50 ml solution of 3.52 mM ctMA and 0.26 M formic acid (electrolyte). ctMA was prepared by heating ccMA at 75° C. for 25 min. The cell was equipped with an Ag/AgCl in sat. KCl reference electrode (Pine) and Pt counter electrode (Pine Research Instruments). The working electrodes were purchased as follows: Sigma (5 wt % Pd/C), Flinn scientific (Cu, Fe, Pb, Zn), Science Company (Ni), and OnlineMetals.com (Ti). Geometric surface areas are displayed in Table 1. Prior to electrocatalysis, the electrodes were cleaned with acetone and MilliQ water, and wiped with a kimwipe. All solutions were magnetically stirred at 400 rpm with a PTFE octagonal stir bar for the duration of the catalytic test. During chronoamperometry experiments, 0.5 ml aliquots of the reaction medium were taken at 5, 15, 30, and 60 min for analysis.

TABLE 1

Geometric dimensions of metal electrodes.

| Metal | Length (mm) | Width (mm) | Thickness (mm) | Area ($cm^2$) |
|---|---|---|---|---|
| Cu | 22.0 | 12.7 | 0.3 | 5.7 |
| Fe | 22.6 | 13.0 | 0.6 | 6.1 |
| Ni | 22.8 | 19.2 | 0.9 | 9.2 |
| Pb | 20.5 | 12.0 | 0.8 | 5.2 |
| Pb (Electropolished) | 20.5 | 11.5 | 0.7 | 5.0 |
| Sn | 22.0 | 13.4 | 0.7 | 6.2 |
| Ti | 23.6 | 11.8 | 1.0 | 6.0 |
| Zn | 20.8 | 11.6 | 0.3 | 5.0 |

Product Analysis.
Samples were diluted 1:1 with MilliQ water (18.0 MΩ) and then analyzed with a Waters Acquity H-Class ultra-performance liquid chromatograph (UPLC) equipped with photodiode array (PDA) and QDa mass detectors. A Waters HSS C18 1.8 μm (2.1×100 mm) column was used to separate ctMA, ttMA, t3HDA, and AA. The MA isomers were quantified with the PDA detector set at 230 nm while t3HDA and AA were quantified with the QDa mass detector in positive and negative mode, respectively. ACS grade ccMA, ttMA, t3HDA, and AA were purchased from Sigma (St Louis, Mo.). These compounds were used for UPLC calibration and as references for NMR analysis.

$^1$H NMR analysis was performed on a Bruker 600 MHz NMR spectrometer (AVIII600). The samples were dried at room temperature under a current of air, reconstituted in deuterium oxide, and subsequently analyzed.

Optical microscopy images were acquired with an EVOS$_{fl}$ light microscope.

Computational Methods.
The geometries were initially optimized using density functional theory (DFT) with the hybrid B3LYP exchange-correlation functional, and the DZVP2 basis set. Vibrational frequencies were calculated to ensure that the optimized structures were minima. The optimized B3LYP/DZVP2 geometries were then used as starting points for G3MP2 calculations to predict gas phase heats of formation ($\Delta H_{gas}$) and the gas phase gas phase acidity ($\Delta G_{gas}$ for the reaction $\Delta H \rightarrow A^- + H^+$). These calculations were done with the Gaussian 09 program system.

The heats of formation of the pure liquid phase were estimated using the fact that the free energy is zero at a phase change so that the enthalpy of vaporization ($\Delta H_{vap}$) can be calculated using $\Delta H_{vap}=T_{BP}\Delta S_{vap}$, where $\Delta H_{vap}$ is the enthalpy of vaporization, Tap is the boiling point in degrees Kelvin (K), and $\Delta S_{vap}$ is the entropy of vaporization. $\Delta S_{vap}$ is approximately constant for many compounds, and thus, for a given boiling point value $\Delta H_{vap}$ can be estimated. It was found that $\Delta S_{vap}=0.031$ cal/mol K. The enthalpy of formation of the pure liquid phase ($\Delta H_{liq}$) is obtained as the difference between the gas enthalpy of formation and the enthalpy of vaporization: $\Delta H_{liq}=\Delta H_{gas}-\Delta H_{vap}$.

The COSMO-RS approach as implemented in the ADF program was used to estimate $T_{BP}$ from DFT results at the B88P86/TZ2P level.

The solvation component for the acidity calculations were done as follows. The solvation free energies in water at 298 K were calculated using the self-consistent reaction field approach with the COSMO parameters, as implemented in the Gaussian 03 using the B3LYP/DZVP2 gas phase geometries. For the COSMO (B3LYP/DZVP2) calculations in Gaussian 03, the radii developed by Klamt and co-workers were used to define the cavity. The aqueous Gibbs free energy (free energy in aqueous solution) ($\Delta G_{aq}$) was calculated from $\Delta G_{aq}=\Delta G_{gas}+\Delta\Delta G_{solv}$ where $\Delta G_{gas}$ is the gas phase free energy and $\Delta\Delta G_{solv}$ is the aqueous solvation free energy calculated as differences between conjugate base and the acid. A dielectric constant of 78.39 corresponding to that of bulk water was used in the COSMO calculations. The solvation energy is reported as the electrostatic energy (polarized solute—solvent). In order to improve the calculated $pK_a$ values, an approach which predicts the $pK_a$ values relative to known standards with $CH_3COOH$ as the reference acid was used. The error in the absolute calculated $pK_a$ of $CH_3COOH$ is 3.0 $pK_a$ units using a value for the free energy of solvation of the proton of $-264.3$ kcal/mol. The $pK_a$ values in aqueous solution relative to $CH_3COOH(HA+CH_3COO^-\rightarrow A^-+CH_3COOH)$ were calculated using: $pK_a=pK_a(CH_3COOH)+\Delta G_{aq}/(2.303\ RT)$.

The calculations were performed on a Xeon-based Dell Linux cluster at the University of Alabama, and a local AMD Opteron-based and Intel Xeon-based Linux cluster from Penguin Computing.

Calculations.

Conversions, selectivities, faradaic efficiencies, dispersion, and turn over frequencies were calculated as shown in Scheme 2. The variable n is the number of electrons transferred (2=HDA, 4=Adipic acid), I is the current transferred, t is the reaction time, and F is Faraday's constant. Cis,trans-muconic acid (ctMA), trans,trans-muconic acid (ttMA), trans-3-hexenedioic acid (t3HDA), and adipic acid (AA), Scheme 2

$$ctMA\ Conversion\ (\%) = \left(1 - \frac{[ctMA]_t}{[ctMA]_0}\right) * 100$$

$$t3HDA\ Selectivity\ (\%) = \frac{[t3HDA]_t}{[ctMA]_0 - [ctMA]_t} * 100$$

$$AA\ Selectivity\ (\%) = \frac{[AA]_t}{[ctMA]_0 - [ctMA]_t} * 100$$

$$ttMA\ Selectivity\ (\%) = \frac{[ttMA]_t}{[ctMA]_0 - [ctMA]_t} * 100$$

Faradaic Efficiency (%) =

$$\frac{\text{Electrons consumed by hydrogenation of organic compounds}}{\text{Total electrons passed}} * 100$$

$$Dispersion\ (\%) = \frac{moles_{Pd\ exposed}}{moles_{Pd}} * 100$$

$$TOF = \frac{moles_{MAconverted}}{moles_{metal} * t}$$

(1-1)(B). Results and Discussion.

Muconic Acid Synthesis and Isomerization.

Figure 2:
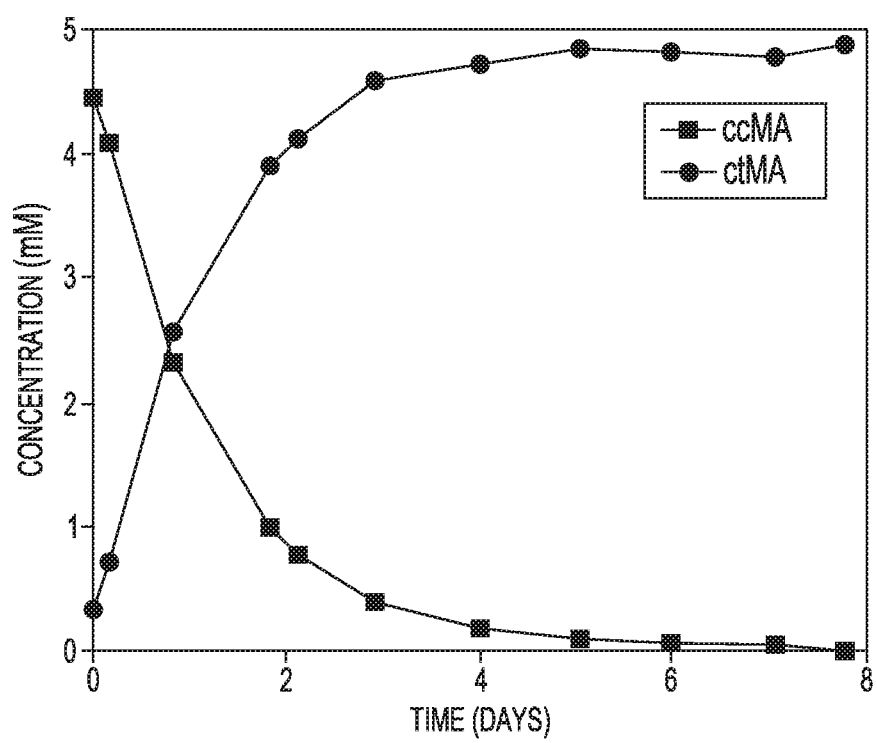
FIG. 2 illustrates concentrations of MA isomers over time at low pH, in accordance with various embodiments.

Biocatalysts selectively produce ccMA by fermentation. The isomerization of ccMA at low pH and under ambient conditions to simulate the ECH conditions was investigated. A 5 mM solution of ccMA and 1.5 mM acetic acid in $D_2O$ was reacted at room temperature for 8 days. FIG. 2 illustrates concentrations of MA isomers over time at low pH. Periodic analysis by $^1H$ NMR revealed that ccMA fully isomerizes into ctMA within 3 days. The composition of the solution remained stable afterwards for at least 5 days. Increasing the temperature to 75° C. allowed the reaction to complete within only 20 min. ttMA was never observed in good agreement with previous work, which stated that ttMA formation requires chemical activation. Given that ccMA production by fermentation typically occurs at temperatures >25° C. for 3-5 days, the present study was carried out using the ctMA isomer as a reactant.

Mechanistic and Thermodynamic Considerations.

ECH and the hydrogen evolution reaction (HER) share the first elemental step (Volmer step), where protons from the solution are reduced to form adsorbed hydrogen atoms (Scheme 3). The adsorbed atoms can then either participate in the electrocatalytic hydrogenation reaction_ or combine to generate $H_2$ following the Tafel or Heyrovsky steps (Scheme 3). Although $H_2$ is a valuable byproduct, its formation is typically undesired during ECH as it lowers the faradaic efficiency (ratio of electrons used for ECH vs HER) and the overall performance of the ECU catalyst. Before any further considerations, it is important to study the thermodynamic equilibria associated with HER and ECH to understand how they evolve with pH and applied potential. Thermodynamic data is widely available for HER. However, muconic acid is not a common reactant and, like many biorenewable molecules, thermodynamic data is not available in the open literature. Therefore, the thermodynamic properties of all the molecules susceptible to form were calculated as well as the heats of formation and the free energies associated with all the hydrogenation reactions that may take place during ECH (Tables 2-3). In all cases, a two-step reaction was considered where MA is first hydrogenated to the corresponding mono-unsaturated di-acid (cis and trans isomers of 2- and 3-HDA) before further hydrogenation to AA (Table 3).

Scheme 3. Volmer, Tafel and Heyrovsky steps.

$H^+ + e^- \rightarrow H_{ads}$ Volmer step (in acid)     (1)

$2H_{ads} \rightarrow H_2$ Tafel step     (2)

$H_{ads} + H^+ + e^- \rightarrow H_2$ Heyrovsky step (in acid)     (3)

Figure 3:
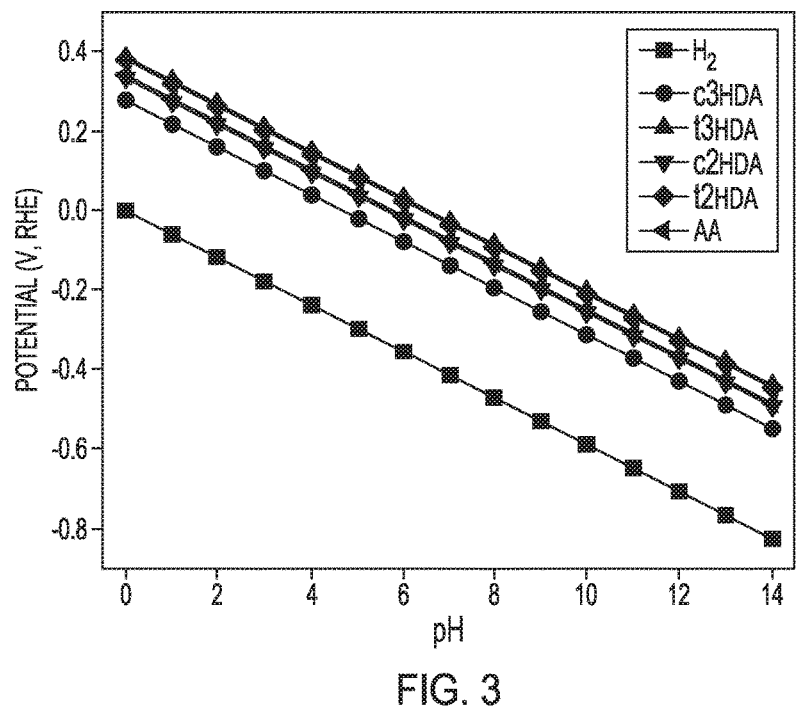
FIG. 3 illustrates theoretical potentials for the formation of hydrogen (HER), cis-3-hexenedioic acid (c3HDA), trans-3-hexenedioic acid (t3HDA), cis-2-hexenedioic acid (c2HDA), trans-2-hexenedioic acid (t2HDA), and AA from cis,trans-muconic acid (ctMA) as a function of pH, in accordance with various embodiments.
Figure 4:
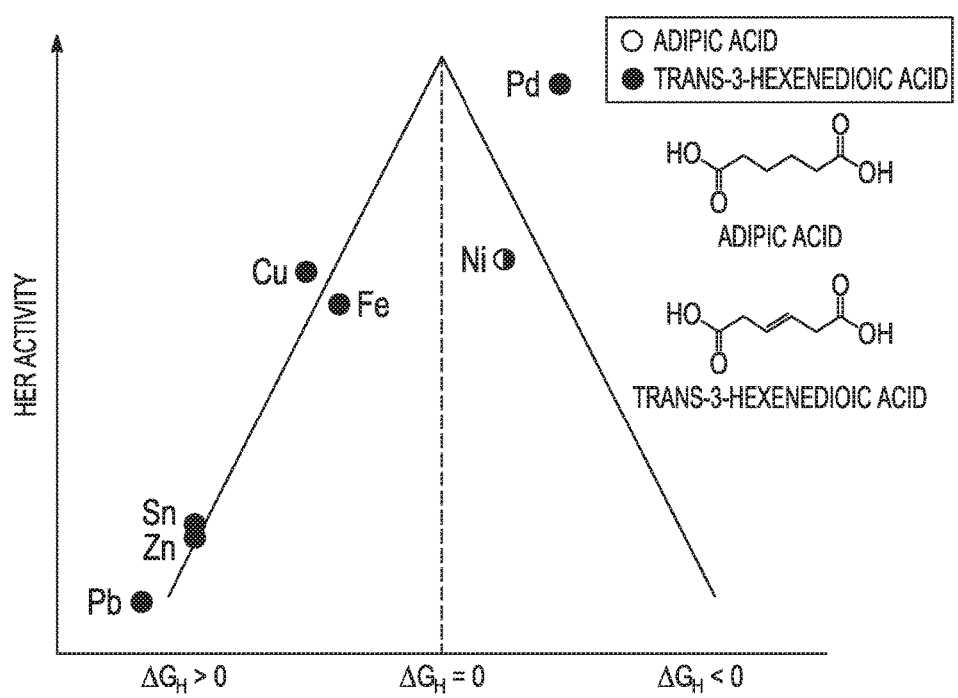
FIG. 4 illustrates a volcano plot showing the current exchange densities (HER activities) achieved as a function of the free energy of hydrogen adsorption $\Delta G_H$ of the metals, in accordance with various embodiments.

As shown in Table 3, all the reactions associated with the hydrogenation of MA to AA are thermodynamically favored by 10 to 20 kcal $mol^{-1}$. These theoretical values can be further used to calculate the theoretical potential of each reaction and its variation with pH using Nernst's equation. FIG. 3 illustrates theoretical potentials for the formation of hydrogen (HER), c3HDA, t3HDA, c2HDA, t2HDA, and AA from ctMA as a function of pH. As shown in FIG. 3, the potentials for ECH are higher than for HER over the pH range 0-14. As HER and ECH are cathodic reactions, FIG. 3 implies that ECH reactions are thermodynamically favored over HER, regardless of pH. The plot also reveals little difference between t2HDA, t3HDA, and AA, meaning that selective synthesis of any of these 3 chemicals by fine tuning the reaction kinetics may be possible. The compounds 2HDA and 3HDA could be useful monomers for polyester and polyamide synthesis based on their structural resemblance to adipic and fumaric acids.

energy for hydrogen binding $\Delta G_H \sim 0$. Metals that bind hydrogen more strongly ($\Delta G_H < 0$) or more weakly ($\Delta G_H > 0$) are significantly less active and adsorbed hydrogen atoms are therefore more likely to be involved in hydrogenation reactions than $H_2$ evolution (FIG. 4). However, at this point it is unclear whether weak ($\Delta G_H > 0$) or strong hydrogen binding ($\Delta G_H < 0$) is best suited for ECH and how large $|\Delta G_H|$ must be to ensure optimal hydrogenation activity. Therefore, a broad range of early, late, and post transition metals representative of both the low and high overpotential metals commonly used for ECH were tested.

TABLE 2

Heats of formation (gas and liquid), boiling point, and gas phase acidities ($\Delta G_{gas}$) at G3MP2 level in kcal mol$^{-1}$ and pK$_a$ (relative to acetic acid).

| Molecule[a] | $\Delta H_f$ (0 K) (gas) | $\Delta H_f$ (298 K) (gas) | BP calc | $\Delta H_{vap,BP}$ | $\Delta H_f$ (298 K) (liq) | $\Delta G_{gas}$ acidity | First pK$_a$ (exp pK$_a$)[b] |
|---|---|---|---|---|---|---|---|
| ccMA | −145.8 | −150.7 | 503.2 | 15.6 | −166.3 | 328.0 | 2.9 |
| ctMA | −146.6 | −151.5 | 569.4 | 17.7 | −169.1 | 328.7 | 2.9 |
| ttMA | −148.8 | −153.6 | 564.1 | 17.5 | −171.0 | 329.0 | 3.4 (2.7) |
| t3HDA | −169.5 | −175.9 | 583.7 | 18.1 | −194.0 | 333.8 | 4.4 (3.96) |
| c3HDA | −168.0 | −175.5 | 584.6 | 18.1 | −193.6 | 329.6 | 4.5 |
| t2HDA | −171.4 | −177.8 | 587.5 | 18.2 | −196.1 | 332.1 | 5.3 |
| c2HDA | −170.2 | −176.8 | 564.9 | 17.5 | −194.3 | 335.2 | 5.9 |
| AA | −197.3 | −205.4 | 586.5 | 18.2 | −223.6 | 335.2 | 5.0 (4.43) |

[a]Notation: ccMA, ctMA, and ttMA correspond to cis,cis-, cis,trans-, and trans,trans-muconic acid; c2HDA, t2HDA, c3HDA, and t3HDA designate the cis (c) and trans (t) isomers of 2-hexenedioic acid (2HDA) and 3-hexenedioic acid (3HDA); AA corresponds to adipic acid.
[b]Experimental pK$_a$ values found in the literature are provided in brackets for comparison.

TABLE 3

Hydrogenation energies at G3MP2 in kcal mol$^{-1}$.

| Reaction[a] | $\Delta H_{gas}$ | $\Delta G_{gas}$ | $\Delta H_{liq}$ | $\Delta G_{aq}$ |
|---|---|---|---|---|
| ccMA + $H_2$ → t3HDA | −24.0 | −17.0 | −27.6 | −20.3 |
| ccMA + $H_2$ → c3HDA | −23.6 | −13.5 | −27.3 | −17.1 |
| ccMA + $H_2$ → t2HDA | −26.0 | −18.4 | −29.7 | −21.9 |
| ccMA + $H_2$ → c2HDA | −24.9 | −17.1 | −28.0 | −19.9 |
| ctMA + $H_2$ → t3HDA | −23.3 | −15.8 | −24.8 | −15.9 |
| ctMA + $H_2$ → c3HDA | −22.9 | −12.3 | −24.5 | −12.7 |
| ctMA + $H_2$ → t2HDA | −25.2 | −17.3 | −26.9 | −17.5 |
| ctMA + $H_2$ → c2HDA | −24.2 | −15.9 | −25.2 | −15.5 |
| ttMA + $H_2$ → t3HDA | −21.2 | −13.8 | −22.9 | −14.3 |
| ttMA + $H_2$ → c3HDA | −20.8 | −10.3 | −22.5 | −11.1 |
| ttMA + $H_2$ → t2HDA | −23.1 | −15.2 | −25.0 | −15.9 |
| ttMA + $H_2$ → c2HDA | −22.1 | −13.9 | −23.3 | −13.9 |
| t3HDA + $H_2$ → AA | −28.4 | −19.3 | −29.7 | −18.8 |
| c3HDA + $H_2$ → AA | −28.8 | −22.7 | −30.0 | −22.1 |
| t2HDA + $H_2$ → AA | −26.5 | −17.8 | −27.6 | −17.3 |
| c2HDA + $H_2$ → AA | −27.5 | −19.1 | −29.3 | −19.3 |

[a]Notation: ccMA, ctMA, and ttMA correspond to cis,cis-, cis,trans-, and trans,trans-muconic acid; c2HDA, t2HDA, c3HDA, and t3HDA designate the cis (c) and trans (t) isomers of 2-hexenedioic acid (2HDA) and 3-hexenedioic acid (3HDA); AA corresponds to adipic acid.

Previous work on ECH revealed that poor HER catalysts offer the highest hydrogenation activities. Unconventional post transition metals such as Pb were particularly selective for levulinic acid and HMF hydrogenation. This observation can be rationalized by analyzing the volcano plot published by S. Trasatti. *Journal of Electroanalytical Chemistry and Interfacial Electrochemistry* 1972, 39, 163-184 and Greeley, J.; Jaramillo, T. F.; Bolide, J.; Chorkendorff, I.; Norskov, J. K. *Nat. Mater.* 2006, 5, 909-913 for HER, shown in FIG. 4. FIG. 4 illustrates a volcano plot showing the current exchange densities (HER activities) achieved as a function of the free energy of hydrogen adsorption $\Delta G_H$ of the metals. Optimal HER activity is achieved for metals with $\Delta G_H \sim 0$. For clarity, only the metals tested in the present work are displayed on the plot. The colors indicate the main product formed during ECH. The highest exchange current densities (high HER activity) were observed for metals with a free ECH with Low Hydrogen Overpotential Metals (Cu, Fe, Ni, Pd).

Figure 5A:
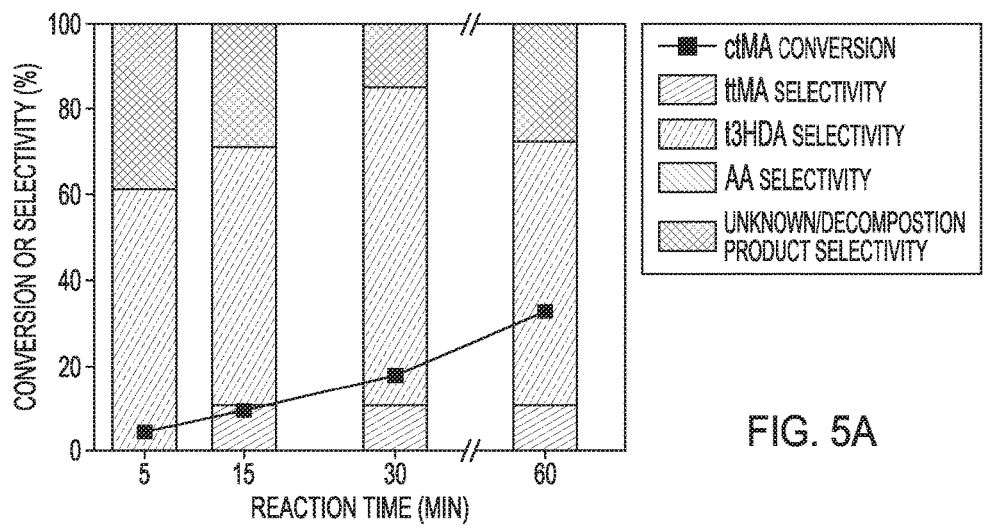
FIGS. 5A-O illustrate conversion, selectivity, and faradaic efficiencies during ECH of ctMA in 1% formic acid solution with various low hydrogen overpotential metals at various voltages, in accordance with various embodiments.
Figure 5B:
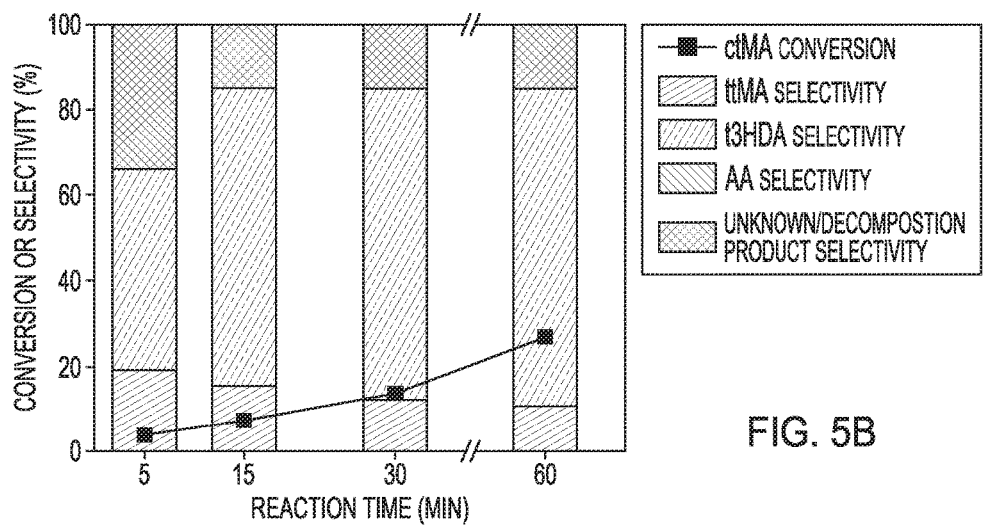
Figure 5C:
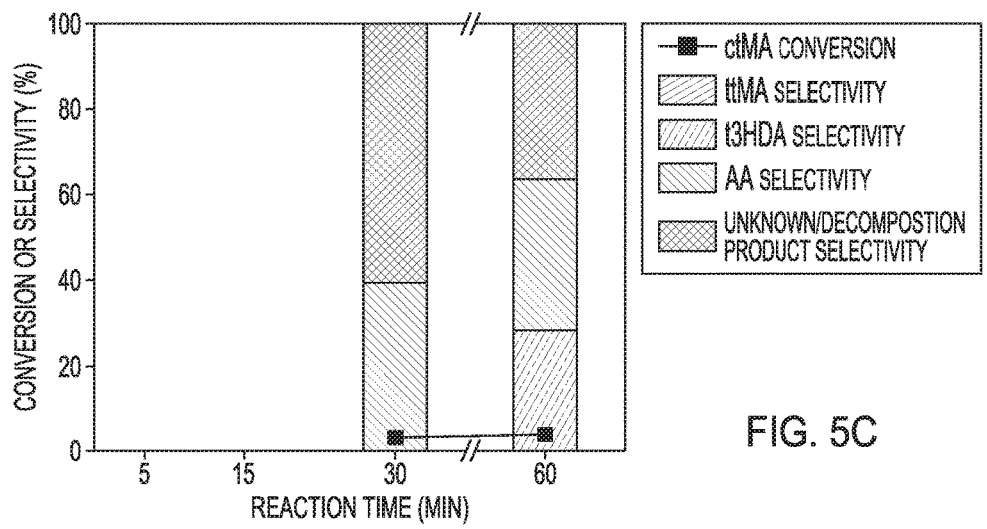
Figure 5D:
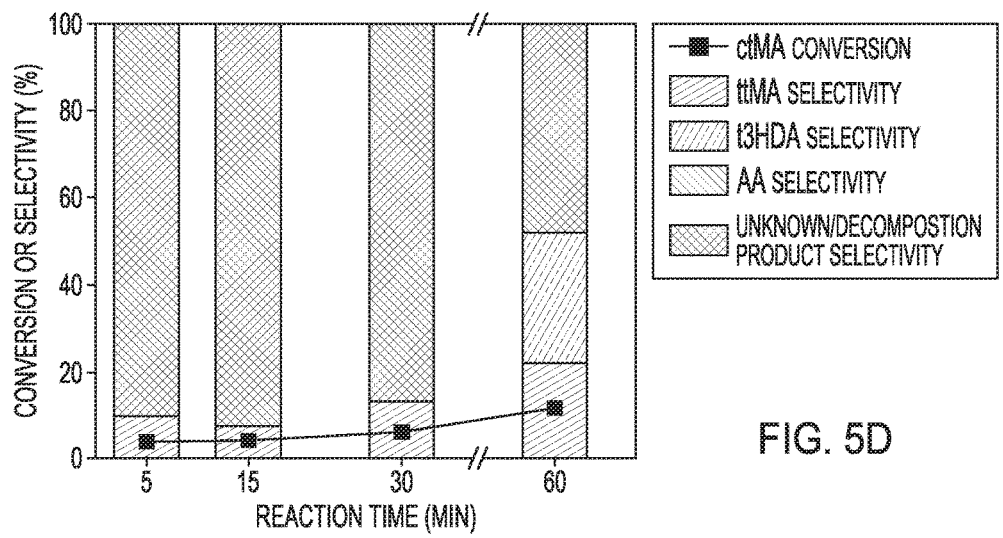
Figure 5E:
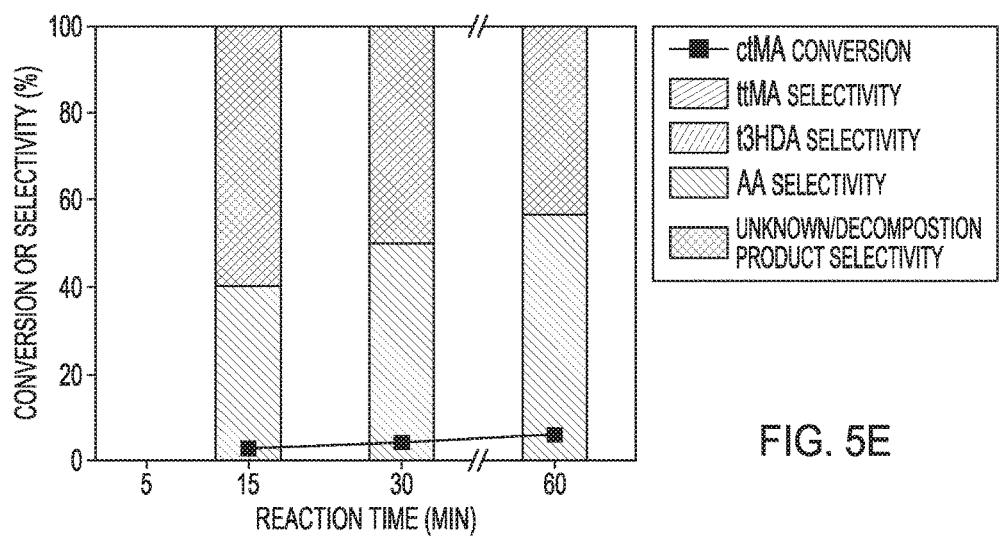
Figure 5F:
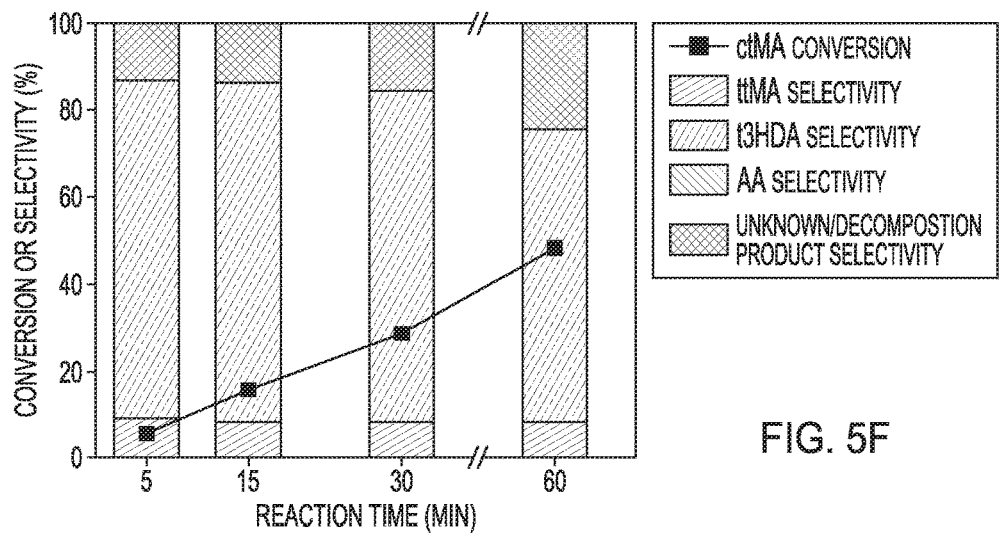
Figure 5G:
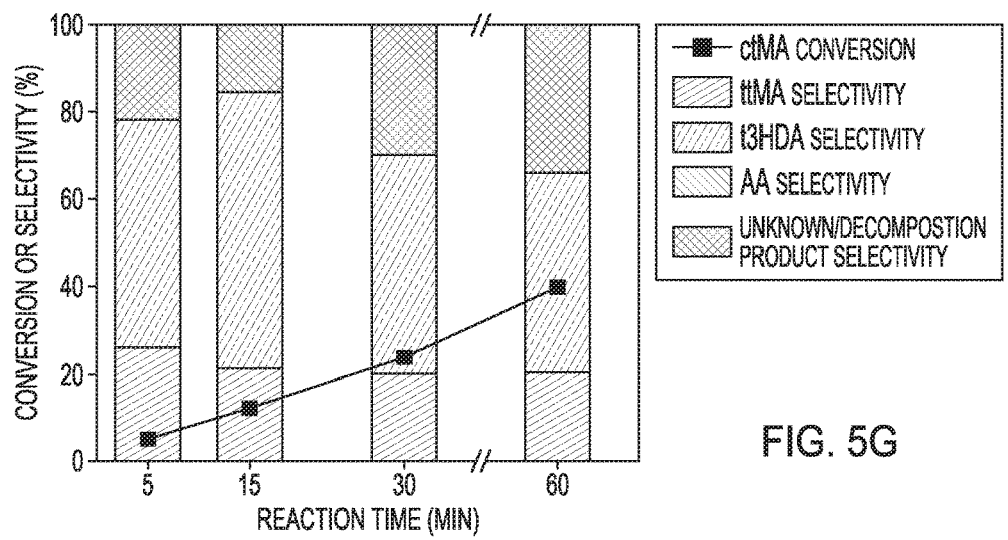
Figure 5H:
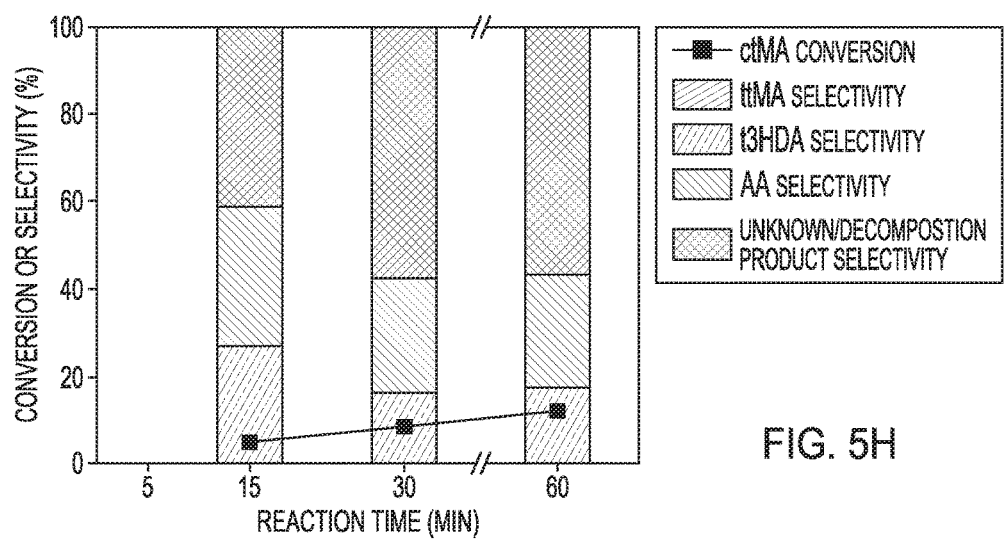
Figure 5I:
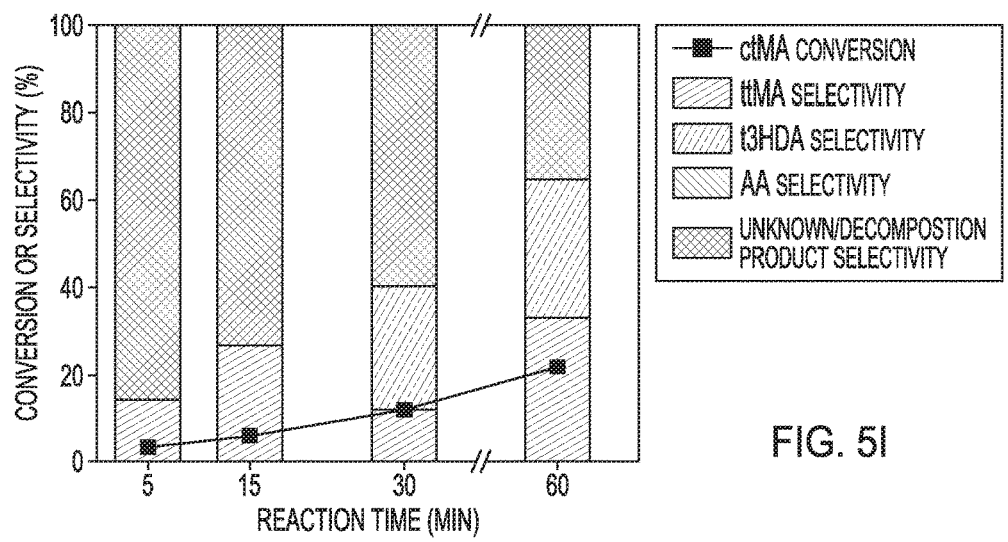
Figure 5J:
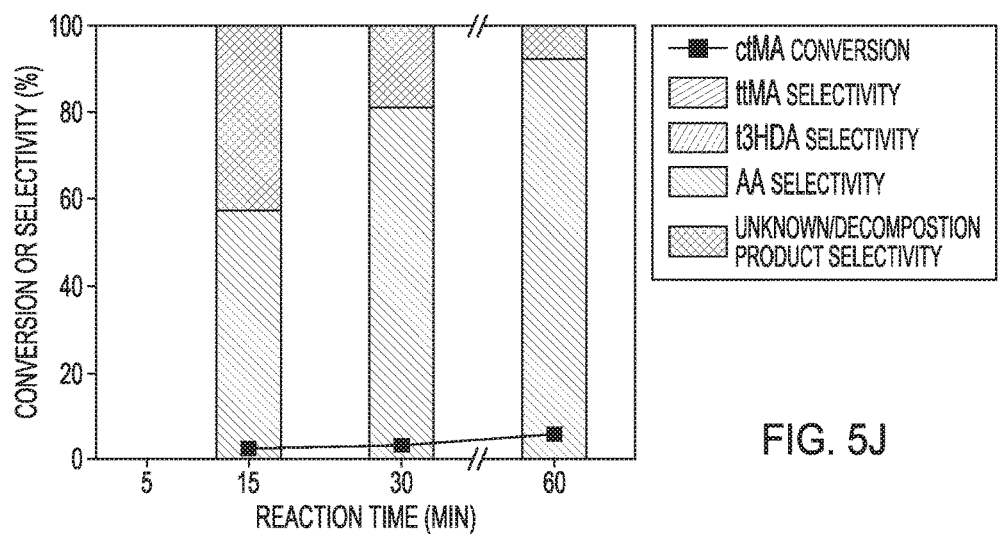
Figure 5K:
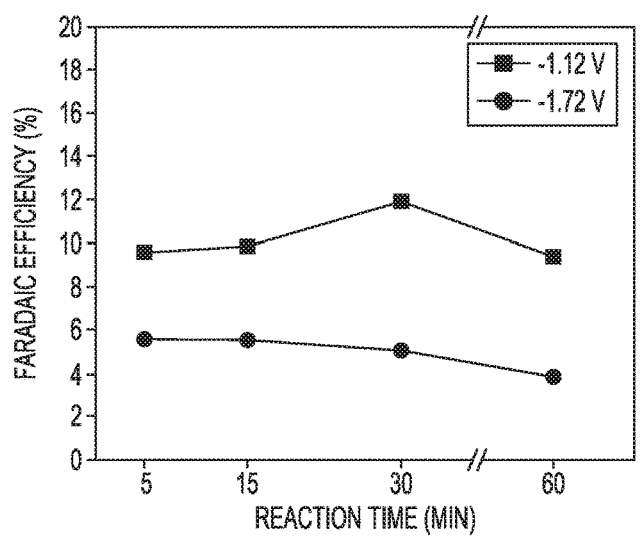
Figure 5L:
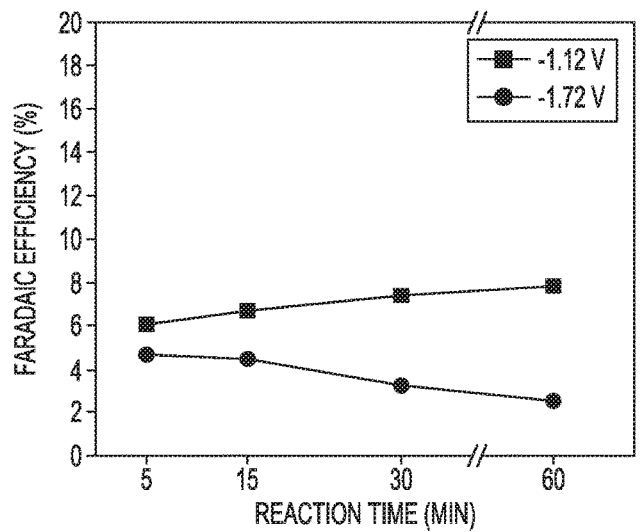
Figure 5M:
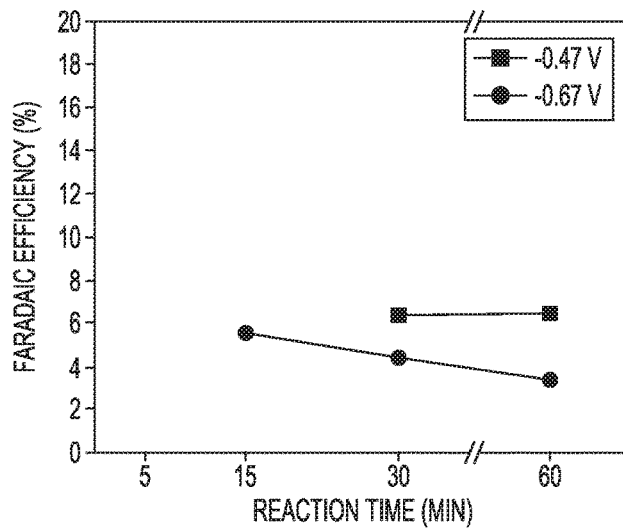
Figure 5N:
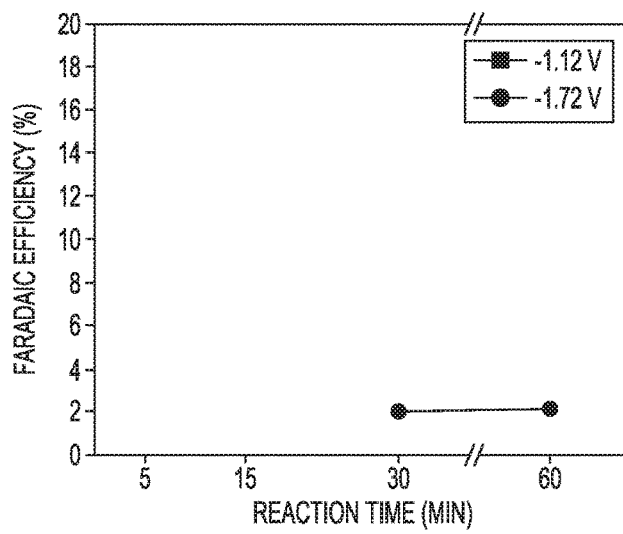
Figure 5O:
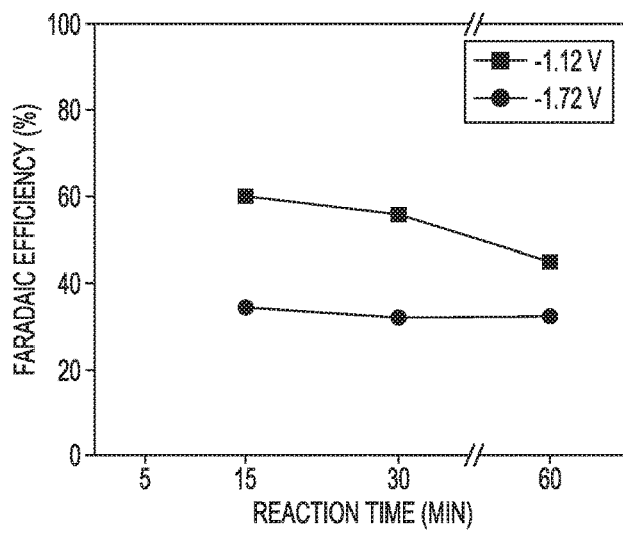

The results obtained for representative low hydrogen overpotential metals are shown in FIGS. 5A-O. FIGS. 5A-O illustrate conversion and selectivity during ECH of ctMA in 1% formic acid solution with low hydrogen overpotential metals at −1.12 V (A, D, G, J, M), −1.72 V (B, E, H, K, K) [with the exception of −0.47 V in G and −0.67 V in H, and faradaic efficiencies (C, F, I, L, O). FIGS. 5A, B, and C used Cu, FIGS. 5D, E, and F used Fe, FIGS. 5G, H, and I used Ni, FIGS. 5J, K and L used Pd foil, and FIGS. 5M, N, and O used Pd/C (5 wt % Pd on C). The catalytic tests for Cu, Fe, Pd, and Pd/C were performed at −1.12 V and −1.72 V vs RHE. However, lower cathodic potentials were applied to the Ni electrode, −0.47 and −0.67 V vs RHE, due to the large HER activity observed above −1.0 V for this metal. In all cases, a solution of 3.52 mM ctMA and 0.26 M formic acid was reacted for 1 h and aliquots of the solution were analyzed by UPLC after 5, 15, 30, and 60 min of reaction. Increasing the cathodic potential from −1.12 V to −1.72 V increased the kinetics of all the electrocatalytic reduction reactions, hence the kinetics of both ECH and HER. While ECH reactions are in general thermodynamically favored over HER (e.g. FIG. 3), the latter is typically faster because fewer elemental steps are involved in the formation of $H_2$ from $H^+$ compared to the hydrogenation reaction. Faradaic efficiencies did not exceed 15% for low hydrogen overpotential metals except Pd/C and generally decreased with increasing muconic acid conversion and hydrogen evolution reactivity as shown in FIGS. 5A-O. These values are consistent with the fact that $H^+$ and ctMA compete to adsorb on the surface of the catalyst and that the concentration of ctMA is two orders of magnitude lower than $[H^+]$.

Low overpotential metals produced both t3HDA and AA. Platinum group metals, specifically Ni and Pd/C, were the only catalysts that produced AA. ECH with Pt was not attempted as platinum is a very active HER catalyst. Pd/C (5 wt % Pd on C) was the best ECH catalyst of this group as it produced AA with 92% selectivity. The fraction of unknown or undetected products calculated based on the carbon balance decreased over time and when increasing the potential from −1.12 V to −1.72 V, thus indicating that ctMA decomposition was minimal and probably only occurred in the early stages of the electrocatalytic reaction. For low overpotential metals with $\Delta G_H\sim 0$, the ECH rate was low compared to HER and the ctMA conversion after 1 h reached 7% at best. The conversions Obtained with Cu and Fe were significantly higher and ranged between 30 and 60% depending on the metal and applied potential. t3HDA was the main product for both catalysts, however, 10-20% ttMA were also detected. ttMA selectivity remained stable for Cu and slightly decreased over the course of the reaction for Fe, which could indicate that ttMA is an intermediate in the hydrogenation of ctMA to t3HDA.

ECH with High Hydrogen Overpotential Metals (Pb, Sn, Ti, Zn).

Figure 6A:
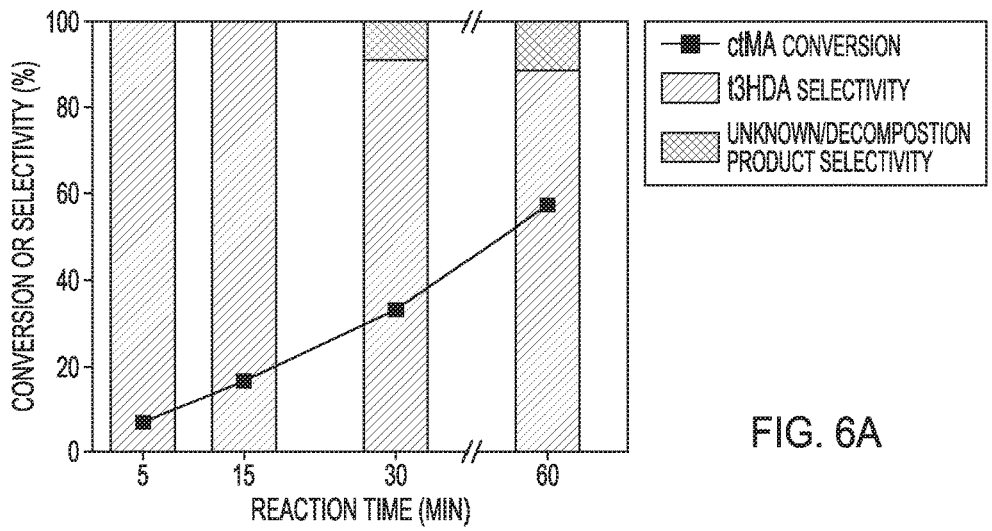
FIGS. 6A-L illustrate conversion, selectivity, and faradaic efficiencies of ECH of ctMA in 1% formic acid solution with various high hydrogen overpotential metals at various voltages, in accordance with various embodiments.

FIGS. 6A-L illustrate conversion and selectivity of ECH of ctMA in 1% formic acid solution with high hydrogen overpotential metals at −1.12 V (A, D, G, J), −1.72 V (B, E, H, K), and corresponding faradaic efficiencies (C, F, I, L). FIGS. 6A, B, and C used Pb, FIGS. 6D, E, and F used Sn, FIGS. 6G, H, I used Ti and FIGS. 6J, K, and L used Zn. Metals that deviate further from ideal HER catalysts and present large $|\Delta G_H|$ were more selective towards t3HDA and showed faster ECH rates than low hydrogen overpotential metals. 40-80% ctMA was converted within 1 h on Ti ($\Delta G_H<0$) and on Pb, Sn, Zn ($\Delta G_H>0$), as shown in FIGS. 6A-L. In contrast to Cu, Fe, Ni, and Pd, ttMA and AA were not detected for this group of transition metals. The selectivity to unknown/decomposition products calculated based on the carbon balance was also lower than for the previous set of catalysts. Finally, late (Zn) and post-transition metals (Pb, Sn) which are on the left side of the volcano plot ($\Delta G_H>0$, see FIG. 4) showed the highest ECH rates and among the highest selectivities to t3HDA. Notably, Ph hydrogenated ctMA to t3HDA with 90% selectivity at 70% conversion under these reaction conditions (FIGS. 6A-L). It should be noted that clear trends between selectivity and hydrogen binding properties have not been identified in previous works. Often, the selectivity towards the desired product is reported at low substrate conversion (<10%), which can be misleading as the selectivity can fluctuate significantly over the course of the reaction, even over short reaction times (FIGS. 6A-L).

ctMA Electrocatalytic Hydrogenation Pathway.

Low and high hydrogen overpotential metals show significant differences in reaction rates and selectivity. The unknown compounds calculated based on the carbon balance could either correspond to additional hydrogenation products that could not be identified and quantified, or to decomposition products resulting from oxidation at the counter electrode. To elucidate more mechanistic detail for the reactions on Pb, the same ECH reaction was performed at low cathodic potential (−0.57 V) to slow the kinetics and monitored the reaction for 300 min. Under these conditions, 57% selectivity towards ttMA was obtained after 60 min of reaction with the Pb electrode. Moreover, ttMA concentration decreased as ctMA conversion reached 80%, thus confirming that ttMA is an intermediate in the hydrogenation of ctMA to t3HDA. This intermediate was not observed at higher potential (−1.12 and −1.72 V) likely due to faster kinetics or a shift in the rate determining step (FIGS. 6A-L).

Figure 7A:
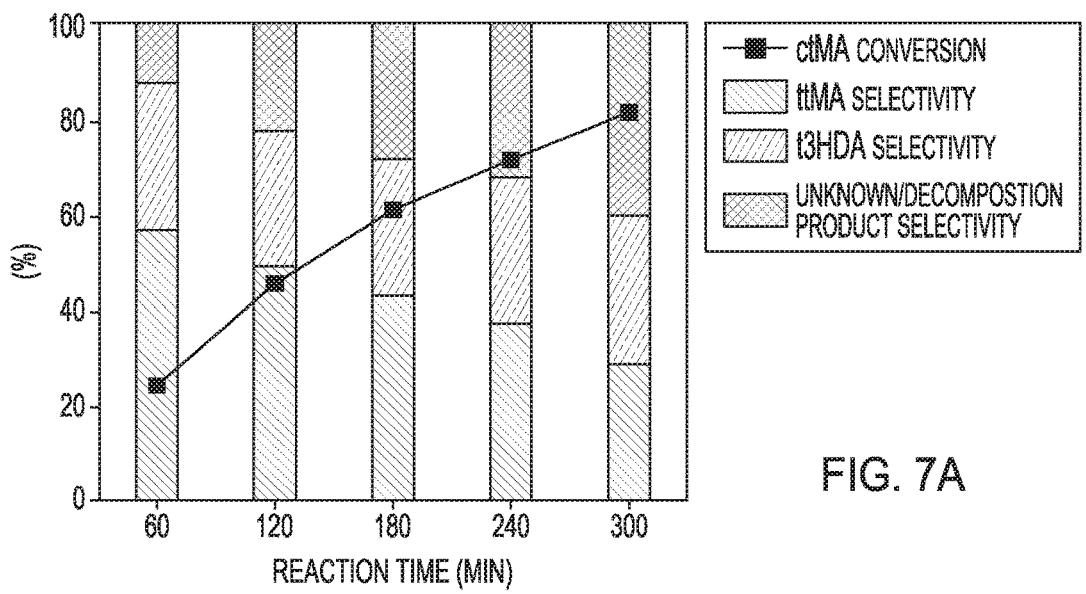
FIG. 7A illustrates ECH an Pb at −0.57 V of ctMA in a 0.01 M sulfuric acid solution, in accordance with various embodiments.
Figure 7B:
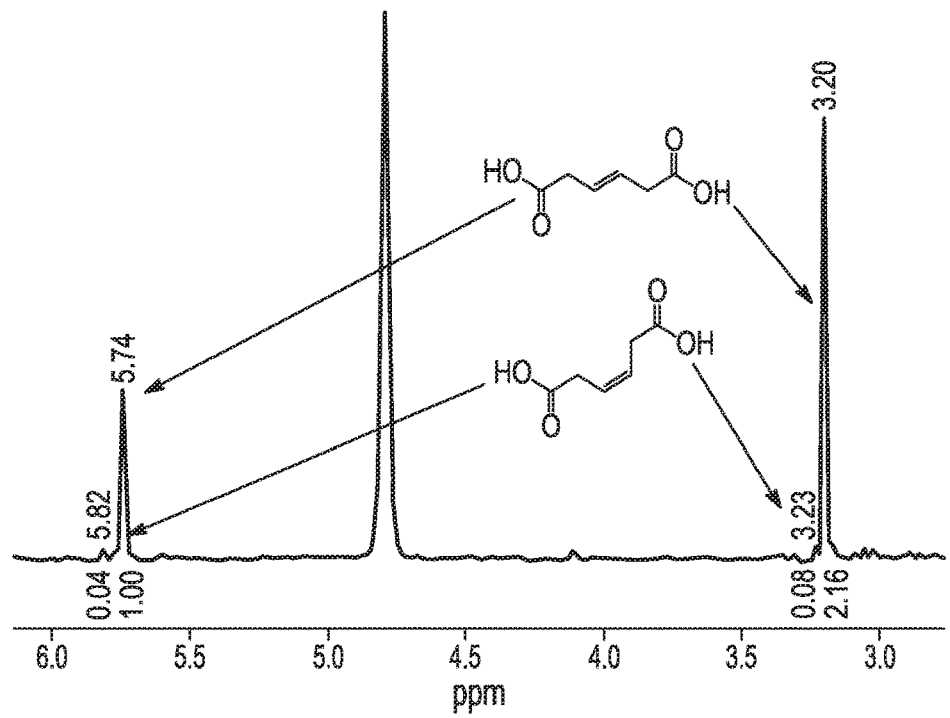
FIG. 7B illustrates a $^1$H NMR spectrum of the reaction products obtained after ECH at −1.72 V, in accordance with various embodiments.
Figure 7C:
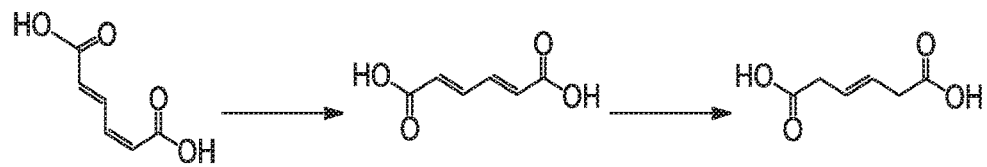
FIG. 7C illustrates a proposed reaction scheme for metals producing t3HDA, in accordance with various embodiments.

FIG. 7A illustrates ECH on Ph at −0.57 V of ctMA in a 0.01 M sulfuric acid solution. FIG. 7B illustrates $^1$H NMR spectrum of the reaction products obtained after ECH a −1.72 V; integrations of c3HDA and t3HDA correspond to 96% geometric isomer selectivity towards t3HDA. FIG. 7C illustrates a proposed reaction scheme for metals producing t3HDA. $^1$H NMR analysis of the solution recovered after ECH of ctMA at −1.72 V displays 96% yield to t3HDA instead of a racemic mixture of cis and trans isomers (FIG. 7B). Further $^1$H NMR analysis of the solution recovered after ECH of t3HDA (substituting ctMA as a reactant) suggests the formation of decomposition products (not shown). For catalysts that produce t3HDA, this suggests that ctMA is first electrochemically isomerized to ttMA followed by the ECH of ttMA to t3HDA (FIG. 7C). It is interesting to note that the further hydrogenation of t3HDA did not occur even with a 600 mV difference in cathodic potential. This could be due to the weaker binding of t3HDA with the metal electrode compared to ctMA and ttMA. Once t3HDA forms and desorbs no further hydrogenation occurs.

The formation of intermediates in the production of AA are less clear. For high-pressure hydrogenation, it was determined that the hydrogenation of MA produced 2HDA followed by subsequent hydrogenation to AA. This result suggests a mechanism involving a 1,2-addition followed by further hydrogenation to AA. Surprisingly, 2HDA was not detected during the synthesis of AA by ECH. Instead, 20-30% of t3HDA, the product of the 1,4-addition, were found during the Ni-catalyzed ECH of ctMA. However, it should be noted that the carbon balance, shown as unknown/decomposition products in FIGS. 5A-O, was significantly lower with Ni and Pd than with other catalysts. The reaction may proceed following two parallel pathways, leading to 2HDA by 1,2-addition and to 3HDA by 1,4-addition. For addition reactions on conjugated dienes, it has been established that the 1,2-adduct forms when the system is under kinetic control while the 1,4-adduct is obtained under thermodynamic control. Therefore, while applying the same potential, it could be possible to either favor the kinetically- or thermodynamically-favored hydrogenation product could be favored depending on the metal catalyst, thus metal-hydrogen bond strength.

Electrochemically Active Surface Area and Turnover Frequency Calculations.

The faradaic efficiency of a reaction is an important measure of hydrogen utilization and a common way to assess the performance of electrocatalysts. While this figure is an important metric, it is highly dependent on reactant concentration, applied potential, and pH of the reacting medium. Another important figure of merit of a catalyst is the turnover frequency (TOE). Despite being a fair value to compare catalysts, TOFs are unusual in electrocatalysis because the electrochemically active surface area (ECSA) is difficult to determine in most cases. Nonetheless, the TOF was estimated for Pb and Pd/C, the most selective catalysts for the production of t3HDA and AA, respectively.

Figure 8A:
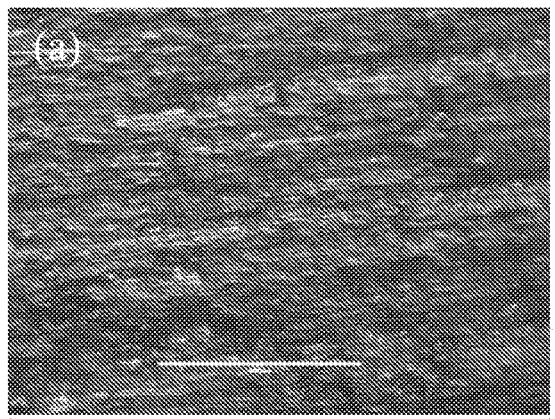
FIGS. 8A-C illustrate light microscope images of the Pb electrode strip (A) after cleaning with a kimwipe, (B) after electropolishing, and (C) after ECH of ctMA, in accordance with various embodiments.
Figure 8B:
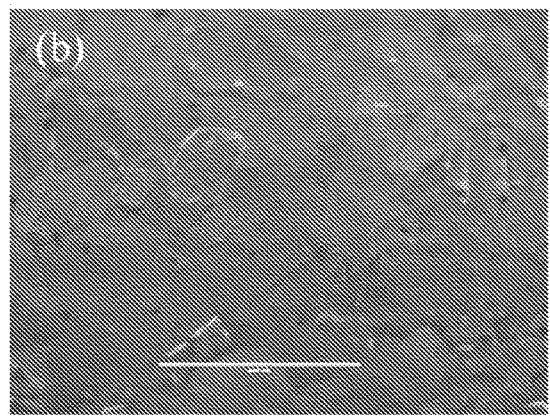
Figure 8C:
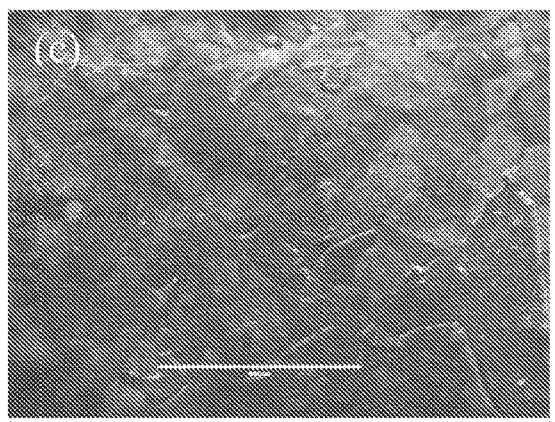
Figure 9A:
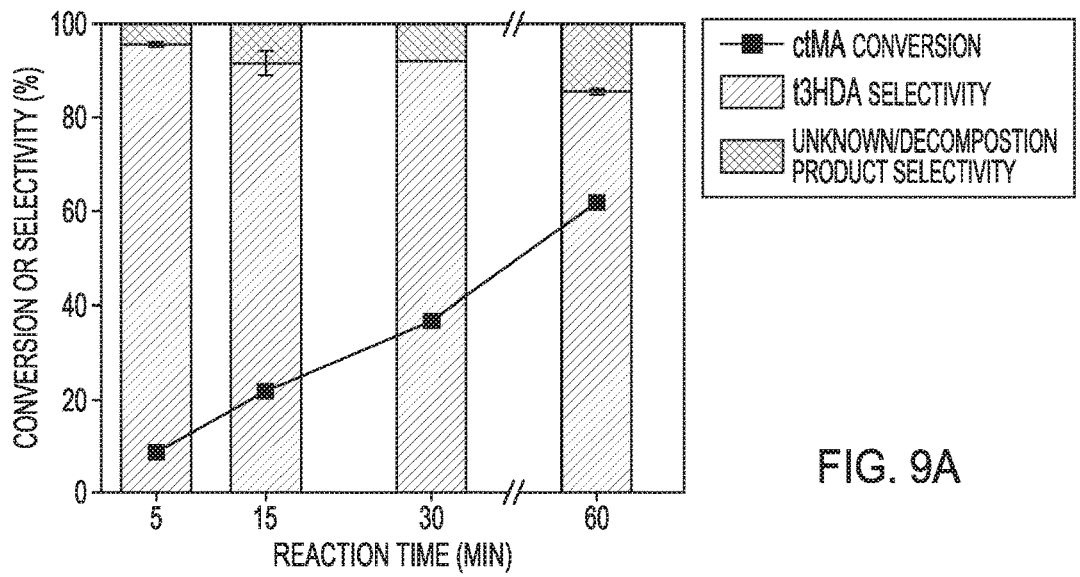
FIGS. 9A-C illustrate conversion (A), selectivity (B), and faradaic efficiency (C) of ECH of ctMA with electro-polished Pb at −1.17 V in a 1% formic acid solution, in accordance with various embodiments.
Figure 9B:
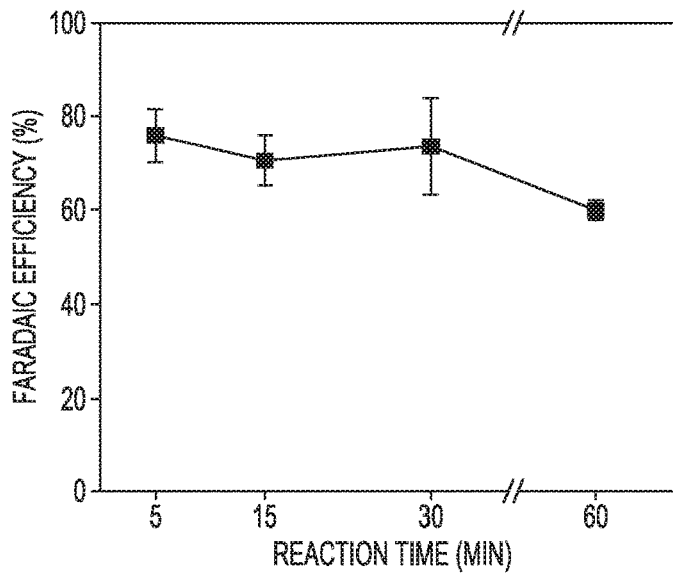
Figure 9C:
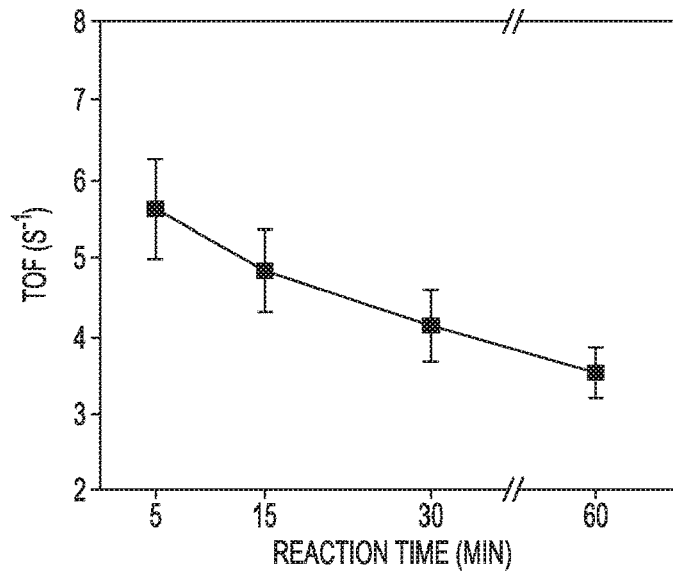

Robust and accurate methods to determine the ECSA of Ph catalysts are not available yet. However, the electrode's surface area can be used directly to estimate the catalyst's TOF if the surface is smooth. Optical microscopy images revealed microscopic features produced through wiping the soft metal with a kimwipe. FIGS. 8A-C illustrate light microscope images of the Ph electrode strip (a) after cleaning with a kimwipe, (b) after electropolishing, and (c) after ECH of ctMA, with the scale bar representing 400 nm. The surface was electropolished by immersing the Pb electrode into an acidic solution and applying a high potential. During this process, burs and sharp edges protruding from the electrode are dissolved into the electrolyte at a faster rate than the oblate material. After electro-polishing, most of these features are leveled and the geometric area of the electrode strip was estimated to be the electrochemically active surface area (FIG. 8B). The number of exposed metal atoms was then calculated using a reference value of 9.39× $10^{14}$ atoms $cm^{-2}$. After electro-polishing, two consecutive ECH of ctMA were carried out and the results were compared. Minor fluctuations in conversion, selectivity, faradaic efficiency, and TOF were calculated although the surface roughness increased (FIG. 8C; error bars in FIGS. 9B-C. FIGS. 9A-C illustrate conversion (A), selectivity (B), and faradaic efficiency (C) of ECH of ctMA with electro-polished Ph at −1.17 V in a 1% formic acid solution. The TOF was of about 6 $s^{-1}$ (rounded from 5.6 $s^{-1}$) in the early stages of the catalytic tests (FIG. 9C). This value seems reasonable considering that it is not based on the ECSA but on the geometric surface area of the electrode.

Figure 10A:
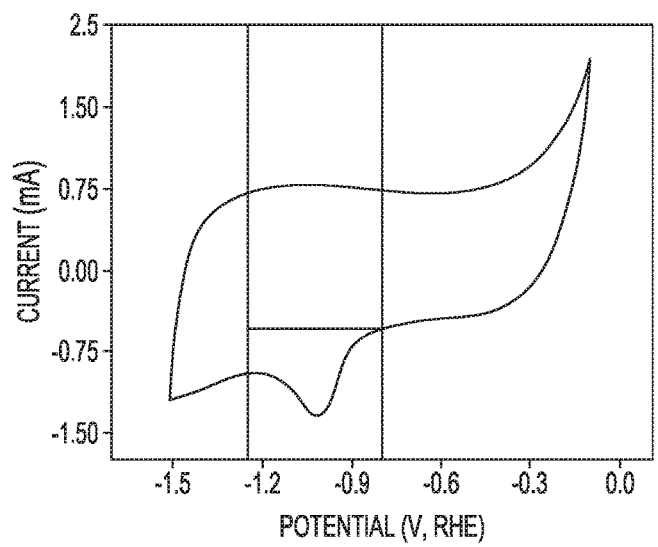
FIG. 10A illustrates cyclic voltammetry of Pd/C in 0.5 M NaOH.
Figure 10B:
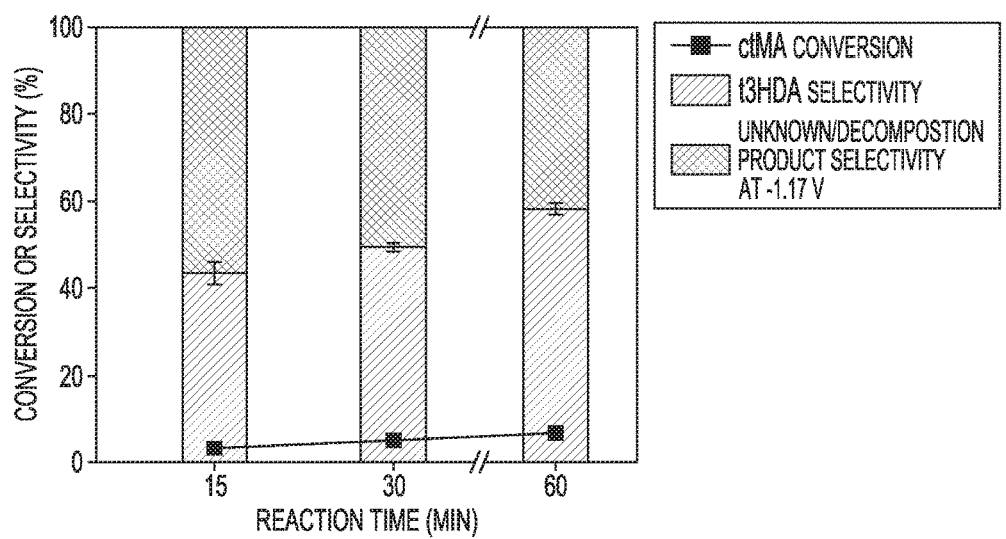
FIG. 10B illustrates conversion and selectivity of ECH of ctMA in 1% formic acid solution at −1.17 V
Figure 10C:
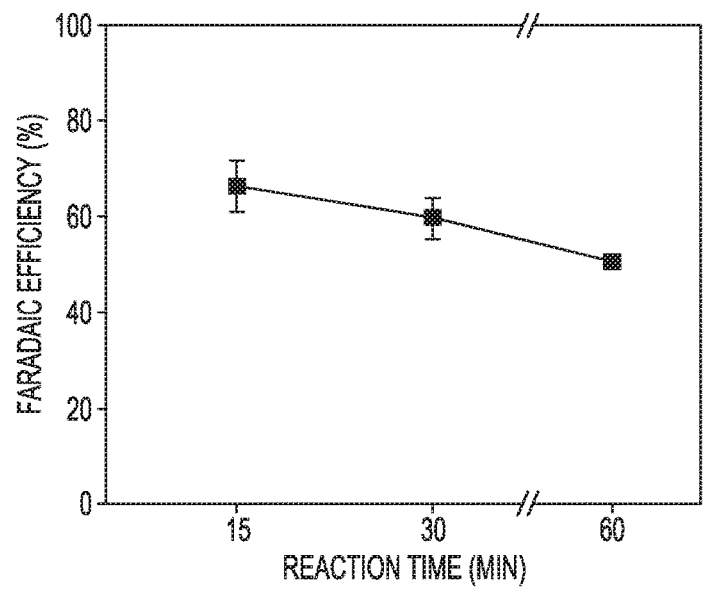
FIG. 10C illustrates the faradaic efficiency during ECH of ctMA in 1% formic acid solution at −1.17 V.
Figure 10D:
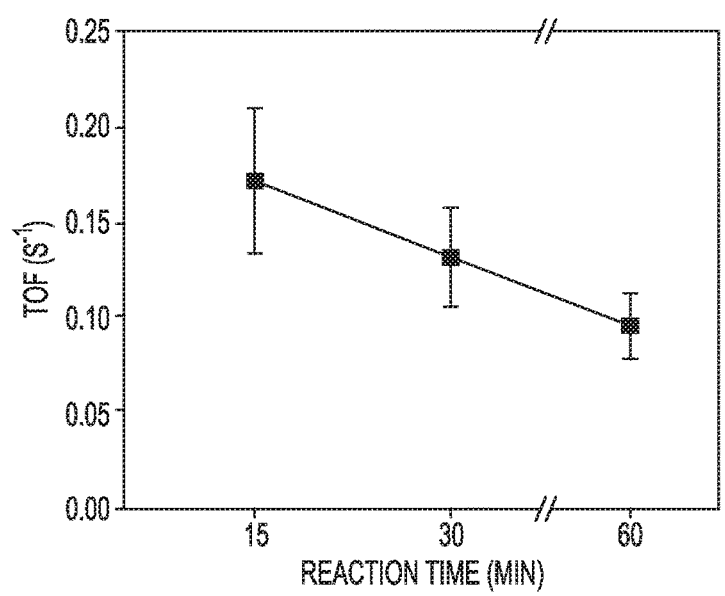
FIG. 10D illustrates the turn over frequency of Pd/C catalyst during ECH of ctMA in 1% formic acid solution at −1.17 V.
Figure 11A:
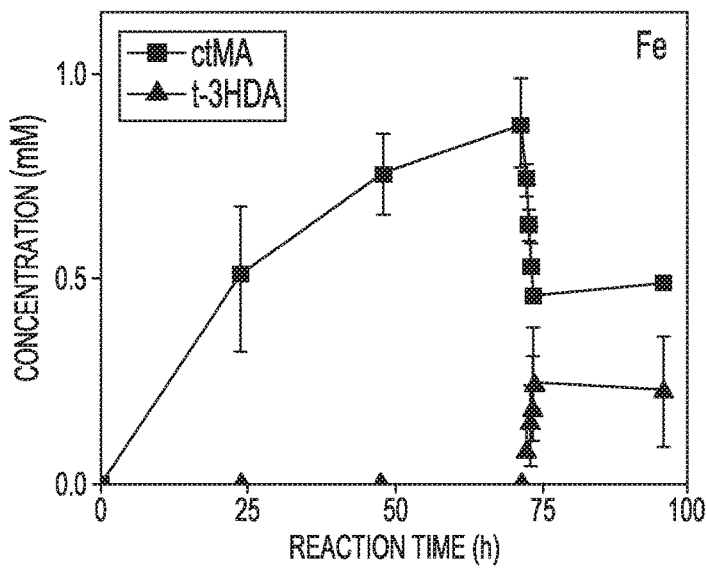
FIGS. 11A-F illustrate ctMA and t3HDA concentration profiles during simultaneous fermentation and ECH, in accordance with various embodiments.
Figure 11B:
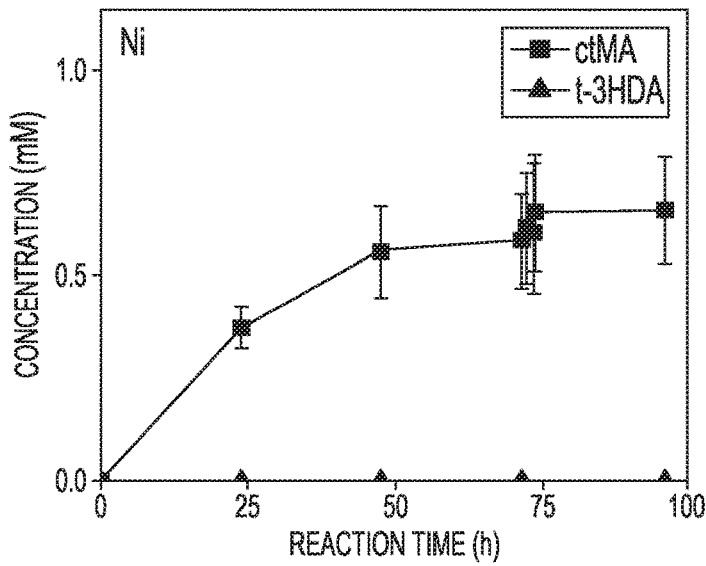
Figure 11C:
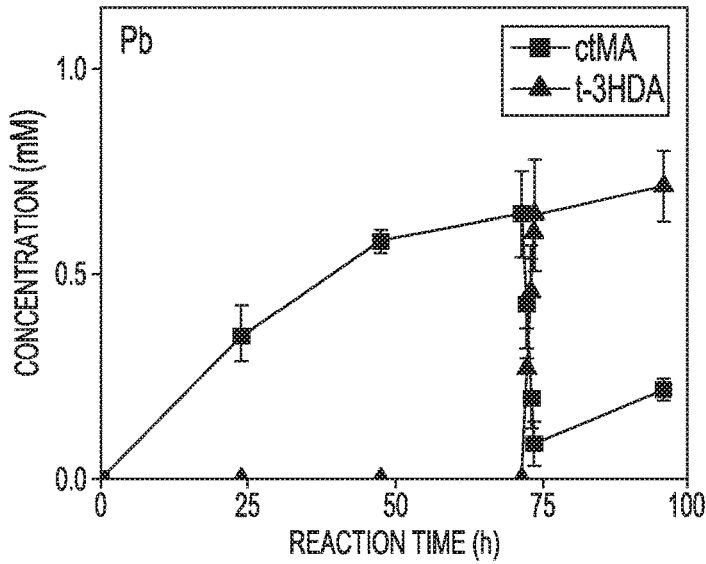
Figure 11D:
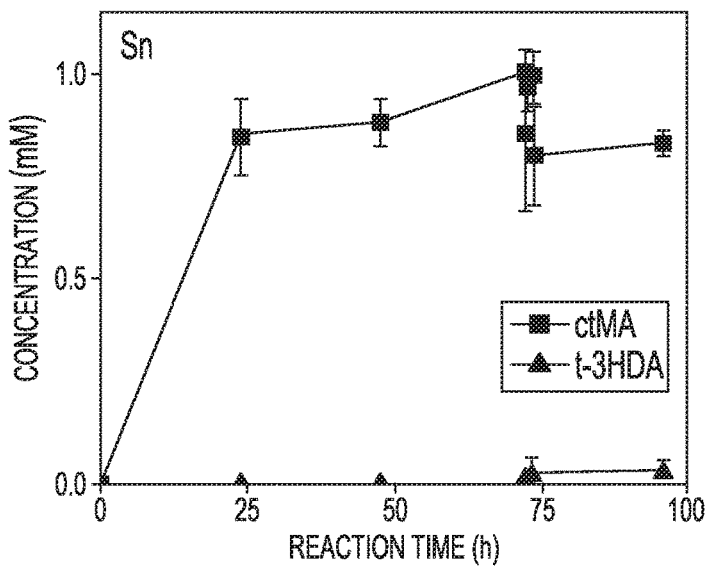
Figure 11E:
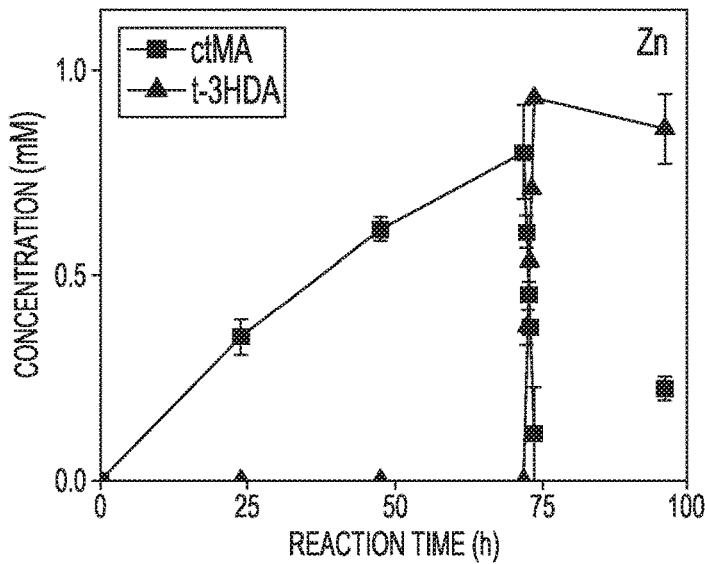
Figure 11F:
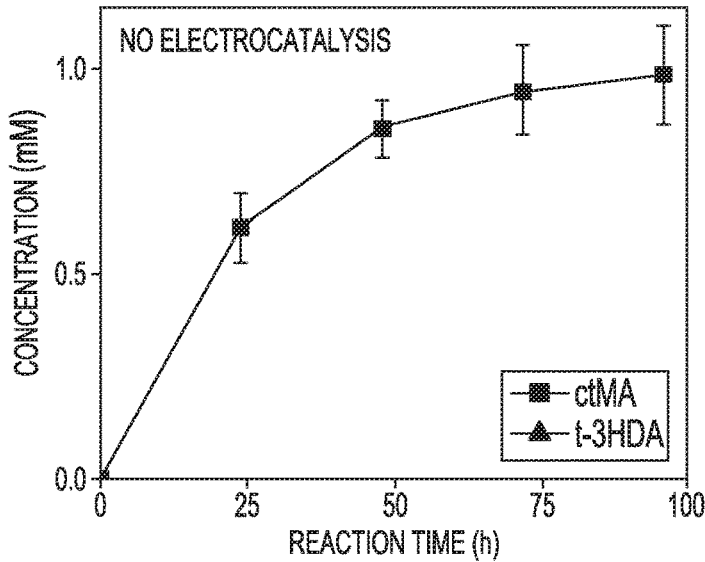

FIGS. 10A-D illustrate (A) Cyclic voltammetry of 5 wt % Pd/C catalyst in 0.5 M NaOH (the peak below the horizontal line is integrated to determine the ECSA); (B) conversion and selectivity of ECH of ctMA in 1% formic acid solution at −1.17 V; (C) the corresponding Faradaic efficiency; and (D) turn over frequency of Pd/C catalyst. The electrochemically active surface area of Pd/C was calculated through the electrochemical oxidation and reduction of Pd in a 0.5 M NaOH solution. In this technique, a monolayer of Pd is oxidized and subsequently reduced. The reduction peak at ca. −1.0 V is then integrated, the electrochemical double layer is subtracted, and the electrochemically active surface area is calculated using a reference value for Pd of 405 μC $cm^{-2}$, and $1.27 \times 10^{15}$ atoms $cm^{-2}$ (FIG. 10A). The value obtained for the Pd/C electrocatalyst was $1.04 \times 10^{-7}$ $mol_{Pd}$ $mg_{cat}^{-1}$, which corresponds to a dispersion of 22±2%. Pd/C exhibited a TOF of 0.15 $s^{-1}$ during the ECH of ctMA (FIG. 10D). In comparison, a TOF of 30 $s^{-1}$ was calculated for Pd/C used for the high pressure hydrogenation of MA to AA. The difference is likely due to the high HER activity of Pd and active site blocking by adsorbed hydrogen.

Simultaneous Fermentation and Hydrogenation.

FIGS. 11A-F illustrate ctMA and t3HDA concentration profiles during simultaneous fermentation and ECH. ECH was performed in the fermentation broth between 72-74 h. A potential of −1.5 V vs. Ag/AgCl was applied to the working electrode during the reaction duration. The working electrodes used in this study corresponds to (A) Fe, (B) Ni, (C) Ph, (D) Sn, and (E) Zn. (F) corresponds to fermentation in absence of ECH.

Conclusions.

The electrocatalytic hydrogenation of MA at room temperature and atmospheric pressure using hydrogen generated in situ from water was explored. ctMA was converted to ttMA, AA, and r3HDA by applying a potential between −0.3 V to −1.8 V on a transition metal catalyst. Conversion, selectivity, and faradaic efficiency were tuned to a large extend by varying the experimental conditions, notably the nature of the metal and the applied potential. The Observed catalytic activities in relation to the hydrogen evolution reaction and thermodynamics were studied. Poor HER catalysts, in particular Pb, were highly active and selective towards t3HDA. It was shown that the reaction proceeds with ttMA as an intermediate and that this bio-based PET precursor can be obtained with a good selectivity by lowering the applied potential. An unexpectedly high TOF of 5.6 $s^{-1}$ was calculated for Pb, a notoriously poor hydrogenation catalyst under conventional high pressure $H_2$ conditions.

Part 2

Example 2-1

(2-1)(A). Materials and Methods.

Lead wire was purchased from rotometals (99.9%) and a lead electrode strip was purchased from EPSI metals (99.999%).

Potassium sulfate was purchased from sigma and sulfuric acid (trace metal grade) was purchased from Millipore.

Cis, Cis-muconic acid (>97%) was purchased from Aldrich. Cis, Trans-muconic acid (ctMA) was synthesized by heating cis, cis-muconic acid (>97%) in water at 75° C. for 25 min. Formic acid (99%) was purchased from. Sigma. All solutions were synthesized in Millipore water (18.0 MΩ).

Calculations for conversion and selectivity are given in Scheme 4.

$$\text{Conversion } MA = \left(1 - \frac{[MA]}{[MA_o]}\right) * 100 \quad \text{Scheme 4}$$

$$\text{Selectivity } ttMA = \frac{[ttMA]}{([MA_o] - [MA])} * 100$$

(2-1)(B). Results and Discussion.

The electrochemical isomerization of muconic acid was carried out in a three-electrode electrochemical cell depicted in FIG. 1. An anodic or cathodic voltage in reference to Ag/AgCl was applied on a variety of different reacting mediums shown in Table 4. Electrochemical isomerizations were attempted with 90 mg $L^{-1}$ or 500 mg $L^{-1}$ ctMA acid using a lead rod or electrode strip as the working electrode. Controlled voltage was applied using a Biologic VSP-300 potentiostat from BioLogic Science Instruments.

Before each experiment, the lead electrode strip was wiped with a kimwipe and the lead wire was scraped with steel wool. The Ag/AgCl reference, Pt counter, and Pb working electrode were subsequently interested into the three-electrode electrochemical cell containing either 50 mL or 15 mL of the aqueous reaction medium, A constant voltage was applied to the reaction mixture for 1.5 h to 5 h. The solution was left at ambient pressure through the reaction. During the experimental duration, 0.5 mL of reaction medium was taken at varying intervals throughout the reaction to analyze product composition. Product conversion and selectivity towards trans,trans-muconic acid acid (ttMA) are displayed in Table 5 at the specified reaction durations.

TABLE 4

| Various reaction mediums. | |
| --- | --- |
| Reaction medium | Reaction medium label |
| Ratio of 0.1M Potassium sulfate and 0.1M Sulfuric acid (pH 2.0) | 1 |
| 0.1M Potassium Hydroxide | 2 |
| 1% formic acid | 3 |

TABLE 5

Isomerization to trans,trans-muconic acid.

| Voltage (V) vs. Ag/AgCl | Reaction Medium | Volume of reactant medium (ml)/ Catalyst used | pH | ctMA conc. (ppm) | Temperature (° C.) | Experimental Duration (h) | Conversion ctMA (%) | Selectivity ttMA (%) |
|---|---|---|---|---|---|---|---|---|
| −0.6 | 1 | 50/Strip | 2 | 90 | Room | 2 | 5 | 30.5 |
| −0.6 | 1 | 15/Rod | 2 | 90 | Room | 1.5 | 44 | 50 |
| −0.525 | 2 | 50/Strip | 14 | 90 | Room | 1.5 | 0 | — |
| −0.95 | 1 | 15/Rod | 2 | 500 | 9 | 1.5 | 0.4 | 35 |
| −1.5 | 1 | 50/Strip | 2 | 500 | 5 | 1.5 | 42 | 0.4 |
| −0.65 | 3 | 50/Strip | 2 | 500 | Room | 2 | 71 | 37 |

Part 3

Example 3-1. Diels-Alder Reactions

At low temperature (120° C. for 3 days) Diels-Alder cycloaddition of ethylene with trans,trans-muconic acid yielded a mixture of cyclohex-1-ene-1,4-diocarboxylic (~70%) and cyclohex-2-ene-1,4-dicarboxylic (~30%) acids due to the ready isomerization from cylcohex-2-ene to cyclohex-1-ene diacids. However, Diels-Alder cycloaddition (75% conversion after 8 hours at 180° C.) in dioxane solvent is 100% selective to cyclohex-2-ene-1,4-dicarboxylic acid without isomerization to cyclohex-1-ene-1,4-dicarboxylic acid. At elevated temperatures or in gamma-valerolactone, cyclohex-1-ene-1,4-dicarboxylic acid is exclusively obtained.

Example 3-2. Diels-Alder Reactions Using Esterified Starting Material

Esterification of trans, trans-muconic acid prior to cycloaddition of ethylene stabilizes the cyclohex-2-ene-1,4-dimethyl ester yielding 93% of the 2 isomer and 7% of the 1 isomer at conversions >99% after 8 hours at 200° C. Esterification of ttMA prior to Diels-Alder yielded the CH2DA dimethyl ester in 93% yield (6% CH1DA dimethyl ester) after 8 hours at 180° C. The choice of solvent becomes inconsequential for Diels-Alder reactions with muconic esters due to an inability to deprotonate and form more stable resonance structures. Furthermore, esterification with a diol prior to cycloaddition is expected to eliminate the need for prepolymerization when preparing polyesters.

Example 3-3. Polyamide

A polyamide was prepared from cyclohex-1-ene-1,4-dicarboxylic acid and hexarnethylenediamine by heating a physical mixture in an inert atmosphere to 200° C. for 30 minutes. The resulting materials had a melting point of 123-130° C. (~60° C. higher than that observed with 3-hexenedioic acid and hexamethylenediamine).

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

ADDITIONAL EMBODIMENTS

The following exemplary embodiments are provided, the numbering of which is not to be construed as designating levels of importance:

Embodiment 1 provides an electrocatalytic method to prepare trans,trans-muconic acid, the method comprising:
passing current through a catalytic cathode in a reactor comprising an aqueous acidic solution comprising cis,trans-muconic acid, a supporting electrolyte, and an anode, so as to isomerize the cis,trans-muconic acid to yield a product comprising trans,trans-muconic acid.

Embodiment 2 provides the method of Embodiment 1, wherein the aqueous acidic solution is substantially free of trans,trans-muconic acid Embodiment 3 provides the method of any one of Embodiments 1-2, wherein the aqueous acidic solution is substantially free of cis,cis-muconic acid.

Embodiment 4 provides the method of any one of Embodiments 1-3, wherein the aqueous acidic solution further comprises the cis,cis-muconic acid.

Embodiment 5 provides the method of any one of Embodiments 1-4, wherein the aqueous acidic solution further comprises trans,trans-muconic acid, wherein the concentration of the trans,trans-muconic acid in the product is higher than the concentration of the trans,trans-muconic acid in the aqueous acidic solution.

Embodiment 6 provides the method of any one of Embodiments 1-5, wherein the cathode comprises one or more transition metals.

Embodiment 7 provides the method of any one of Embodiments 1-6, wherein the cathode consists of one or more transition metals.

Embodiment 8 provides the method of any one of Embodiments 1-7, wherein the cathode comprises one or more platinum group metals.

Embodiment 9 provides the method of any one of Embodiments 1-8, wherein the cathode consists of one or more platinum group metals.

Embodiment 10 provides the method of any one of Embodiments 1-9, wherein the cathode comprises at least one of Cu, Fe, Ni, Pd, Pt, Pd C, Pb, Sn, Ti, Zn, or a combination thereof.

Embodiment 11 provides the method of any one of Embodiments 1-10, wherein the cathode comprises Pb.

Embodiment 12 provides the method of any one of Embodiments 1-11, wherein the cathode consists of Pb.

Embodiment 13 provides the method of any one of Embodiments 1-12, wherein the cis,trans-muconic acid is converted to the trans,trans-muconic acid with a selectivity of about 0.01% to about 100%.

Embodiment 14 provides the method of any one of Embodiments 1-13, wherein the cis,trans-muconic acid is converted to the trans,trans-muconic acid with a selectivity of about 25% to about 60%.

Embodiment 15 provides the method of any one of Embodiments 1-14, wherein the cis,trans-muconic acid is converted to the trans,trans-muconic acid with a conversion of about 0.01% to about 100%.

Embodiment 16 provides the method of any one of Embodiments 1-15, wherein the cis,trans-muconic acid is converted to the trans,trans-muconic acid with a conversion of about 35% to about 80%.

Embodiment 17 provides the method of any one of Embodiments 1-16, wherein the isomerization is performed for about 1 minute to about 24 hours.

Embodiment 18 provides the method of any one of Embodiments 1-17, wherein the isomerization is performed for about 1 hour to about 6 hours.

Embodiment 19 provides the method of any one of Embodiments 1-18, wherein the aqueous acidic solution comprises an organic, acid, a mineral acid, a salt thereof, or a combination thereof.

Embodiment 20 provides the method of any one of Embodiments 1-19, wherein the aqueous acidic solution comprises formic acid, sulfuric acid, a salt thereof, or a combination thereof.

Embodiment 21 provides the method of any one of Embodiments 1-20, wherein the aqueous acidic solution comprises a salt of an organic acid, a salt of a mineral acid, or a combination thereof.

Embodiment 22 provides the method of any one of Embodiments 1-21, wherein the aqueous acidic solution comprises a sulfate salt, a formate salt, or a combination thereof.

Embodiment 23 provides the method of any one of Embodiments 1-22, wherein the aqueous acidic solution comprises potassium sulfate, potassium formate, or a combination thereof.

Embodiment 24 provides the method of any one of Embodiments 1-23, wherein the current is generated by applying a voltage of about −0.3 V to about −3.0 V with respect to an Ag/AgCl reference electrode or with respect to a reversible hydrogen electrode.

Embodiment 25 provides the method of any one of Embodiments 1-24, wherein the current is generated by applying a voltage of about −0.5 V to about −1.5 V with respect to an Ag/AgCl reference electrode or with respect to a reversible hydrogen electrode.

Embodiment 26 provides the method of any one of Embodiments 1-25, wherein the isomerization is carried out at about ambient temperature and pressure.

Embodiment 27 provides the method of any one of Embodiments 1-26, wherein the aqueous solution comprises an acidic fermentation broth comprising the cis,trans-muconic acid.

Embodiment 28 provides the method of Embodiment 27, wherein the fermentation broth comprises glucose and supports the conversion of glucose into muconic acid by yeast.

Embodiment 29 provides the method of any one of Embodiments 27-28, wherein the fermentation broth comprises yeast nitrogen base.

Embodiment 30 provides the method of Embodiment 29, wherein the yeast nitrogen base is substantially free of amino acids, ammonium sulfate, or a combination thereof.

Embodiment 31 provides the method of any one of Embodiments 27-30, wherein the fermentation broth comprises ammonium sulfate.

Embodiment 32 provides the method of any one of Embodiments 27-31, wherein the fermentation broth comprises complete supplement mixture (CSM) uracil-dropout amino acid mix.

Embodiment 33 provides the method of any one of Embodiments 27-32, wherein the method comprises at least partially simultaneously fermenting the broth to form cis, trans-muconic acid and isomerizing cis,trans-muconic acid in the broth.

Embodiment 34 provides the method of any one of Embodiments 1-33, further comprising reacting the trans, trans-muconic acid with a Diels-Alder dienophile to form a Diels-Alder adduct.

Embodiment 35 provides the method of Embodiment 34, wherein the Diels-Alder reaction is performed at elevated temperatures, in γ-valerolactone (GVL), or in dioxane, the dienophile is a substituted or unsubstituted ethylene, and the Diels-Alder adduct is a substituted or unsubstituted cyclohex-1-ene-1,4-dicarboxylic acid and no substituted or unsubstituted cyclohex-2-ene-1,4-dicarboxylic acid is formed.

Embodiment 36 provides the method of any one of Embodiments 34-35, wherein the dienophile is a substituted or unsubstituted ethylene, wherein the Diels-Alder adduct is a tetrahydrogenated substituted or unsubstituted terephthalic acid.

Embodiment 37 provides the method of any one of Embodiments 34-56, further comprising aromatizing the Diels-Alder adduct, to provide an aromatic compound.

Embodiment 38 provides the method of any one of Embodiments 34-37, wherein the dienophile is a substituted or unsubstituted ethylene, further comprising aromatizing the Diels-Alder adduct, to provide substituted or unsubstituted terephthalic acid.

Embodiment 39 provides the method of any one of Embodiments 34-38, wherein the dienophile is ethylene, further comprising aromatizing the Diels-Alder adduct, to provide terephthalic acid.

Embodiment 40 provides the method of any one of Embodiments 38-39, further comprising polymerizing the substituted or unsubstituted terephthalic acid with ethylene glycol, to provide substituted or unsubstituted polyethylene terephthalate.

Embodiment 41 provides the method of any one of Embodiments 38-40, wherein the aromatizing is performed using reactants comprising Pd/C.

Embodiment 42 provides the method of any one of Embodiments 1-41, further comprising esterifying the trans, trans-muconic acid and reacting the esterification product with a Diels-Alder dienophile to form a Diels-Alder adduct.

Embodiment 43 provides the method of Embodiment 42, wherein the dienophile is a substituted or unsubstituted ethylene, and the Diels-Alder adduct is a substituted or unsubstituted cyclohex-2-ene-1,4-dicarboxylic acid and no substituted or unsubstituted cyclohex-1-ene-1,4-dicarboxylic acid is formed.

Embodiment 44 provides an electrocatalytic method to prepare trans,trans-muconic acid from cis,trans-muconic acid, the method comprising:

passing current through a catalytic cathode comprising Pb, wherein the catalytic cathode is in a reactor comprising an aqueous acidic solution comprising cis,trans-muconic acid, a supporting electrolyte, and an anode, so as to isomerize the muconic acid to yield a product comprising trans,trans-muconic acid.

Embodiment 45 provides an electrocatalytic method to prepare terephthalic acid from cis,trans-muconic acid, the method comprising:

passing current through a catalytic cathode in a reactor comprising an aqueous acidic solution comprising cis,trans-muconic acid, a supporting electrolyte, and an anode, so as isomerize the cis,trans-muconic acid to yield a product comprising trans,trans-muconic acid;

reacting the trans,trans-inuconic acid with ethylene to form a Diels-Alder adduct; and aromatizing the Diels-Alder adduct, to provide terephthalic acid.

Embodiment 46 provides the method of any one or any combination of Embodiments 1-45 optionally configured such that all elements or options recited are available to use or select from.

What is claimed is:

1. An electrocatalytic method to prepare trans,trans-muconic acid, the method comprising:
passing current through a catalytic cathode in a reactor comprising an aqueous acidic solution comprising cis, trans-muconic acid, a supporting electrolyte, and an anode, so as to isomerize the cis,trans-muconic acid to yield a product comprising trans,trans-muconic acid;
wherein the aqueous solution is free of organic solvent.

2. The method of claim 1, wherein the cathode comprises at least one of Cu, Fe, Ni, Pd, Pt, Pd/C, Pb, Sn, Ti, Zn, or a combination thereof.

3. The method of claim 1, wherein the cathode comprises Pb.

4. The method of claim 1, wherein the aqueous acidic solution further comprises an organic acid, a mineral acid, a salt thereof, or a combination thereof.

5. The method of claim 1, wherein the aqueous acidic solution further comprises potassium sulfate, potassium formate, or a combination thereof.

6. The method of claim 1, wherein the current is generated by applying a voltage of about −0.3 V to about −3.0 V with respect to an Ag/AgCl reference electrode or with respect to a reversible hydrogen electrode.

7. The method of claim 1, wherein the aqueous solution further comprises an acidic fermentation broth comprising the cis,trans-muconic acid.

8. The method of claim 7, wherein the fermentation broth further comprises glucose and supports the conversion of glucose into muconic acid by yeast.

9. The method of claim 7, wherein the fermentation broth further comprises yeast nitrogen base.

10. The method of claim 7, wherein the fermentation broth further comprises ammonium sulfate.

11. The method of claim 7, wherein the fermentation broth further comprises complete supplement mixture (CSM) uracil-dropout amino acid mix.

12. The method of claim 7, wherein the method further comprises at least partially simultaneously fermenting the broth to form cis,trans-muconic acid and isomerizing cis, trans-muconic acid in the broth.

13. The method of claim 1, further comprising reacting the trans,trans-muconic acid with a Diels-Alder dienophile to form a Diels-Alder adduct.

14. The method of claim 13, further comprising aromatizing the Diels-Alder adduct, to provide an aromatic compound.

15. The method of claim 13, wherein the dienophile is a substituted or unsubstituted ethylene, further comprising aromatizing the Diels-Alder adduct, to provide substituted or unsubstituted terephthalic acid.

16. The method of claim 15, further comprising polymerizing the terephthalic acid with ethylene glycol, to provide polyethylene terephthalate.

17. The electrocatalytic method of claim 1, wherein the method further comprises:
reacting the trans,trans-muconic acid with ethylene to form a Diels-Alder adduct; and
aromatizing the Diels-Alder adduct, to provide terephthalic acid.

18. The method of claim 1, wherein the aqueous acidic solution further comprises formic acid, sulfuric acid, a salt thereof, or a combination thereof.

19. The method of claim 1, wherein the aqueous acidic solution further comprises a muconic acid starting material comprising the cis,trans-muconic acid wherein cis,cis-muconic acid is less than 5 mol % of the muconic acid starting material.

20. The method of claim 1, wherein the reactor further comprises a three-electrode electrochemical cell comprising the aqueous acidic solution comprising cis,trans-muconic acid, the supporting electrolyte, and the anode.

* * * * *

UNITED STATES PATENT AND TRADEMARK OFFICE
CERTIFICATE OF CORRECTION

PATENT NO. : 10,465,043 B2
APPLICATION NO. : 15/348122
DATED : November 5, 2019
INVENTOR(S) : Tessonnier et al.

Page 1 of 4

It is certified that error appears in the above-identified patent and that said Letters Patent is hereby corrected as shown below:

On the Title Page

In item (73), in "Assignee", in Column 1, Line 2, after "Foundation,", insert --Inc.,--

In item (57), in "Abstract", in Column 2, Lines 8-9, delete "trans trans-muconic" and insert --trans,trans-muconic-- therefor In the Drawings On sheet 3 of 18, Fig. 5A, delete "UNKNOWN/DECOMPOSTION" and insert --UNKNOWN/DECOMPOSITION-- therefor On sheet 3 of 18, Fig. 5B, delete "UNKNOWN/DECOMPOSTION" and insert --UNKNOWN/DECOMPOSITION-- therefor On sheet 3 of 18, Fig. 5C, delete "UNKNOWN/DECOMPOSTION" and insert --UNKNOWN/DECOMPOSITION-- therefor On sheet 4 of 18, Fig. 5D, delete "UNKNOWN/DECOMPOSTION" and insert --UNKNOWN/DECOMPOSITION-- therefor On sheet 4 of 18, Fig. 5E, delete "UNKNOWN/DECOMPOSTION" and insert --UNKNOWN/DECOMPOSITION-- therefor On sheet 4 of 18, Fig. 5F, delete "UNKNOWN/DECOMPOSTION" and insert --UNKNOWN/DECOMPOSITION-- therefor On sheet 5 of 18, Fig. 5G, delete "UNKNOWN/DECOMPOSTION" and insert --UNKNOWN/DECOMPOSITION-- therefor Signed and Sealed this
Twenty-second Day of September, 2020

Andrei Iancu
*Director of the United States Patent and Trademark Office*

CERTIFICATE OF CORRECTION (continued)
U.S. Pat. No. 10,465,043 B2

Figure 6B:
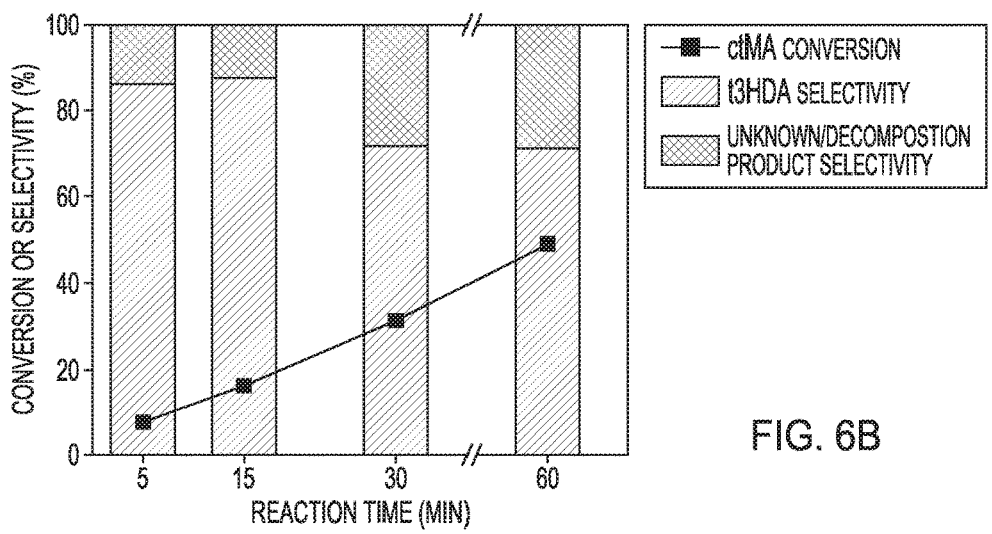
Figure 6C:
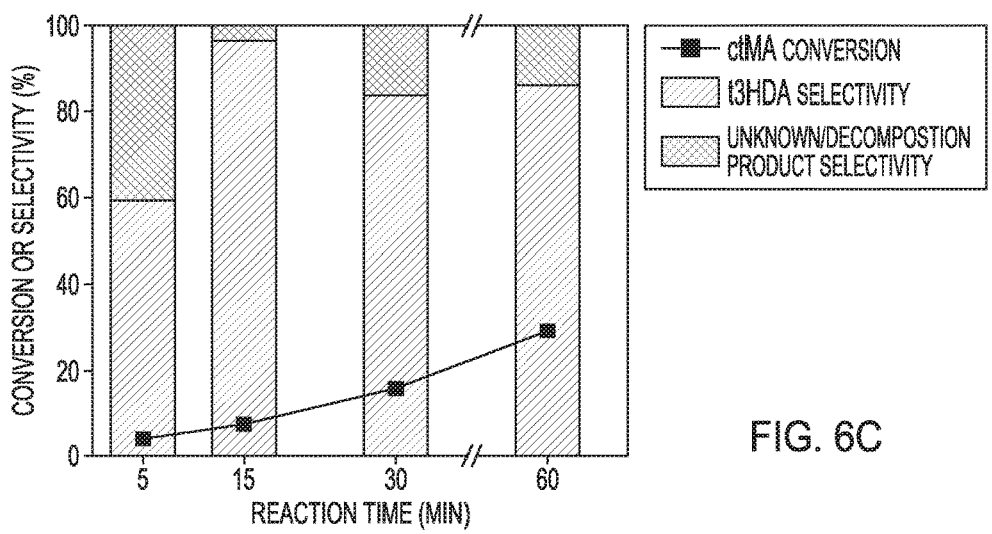
Figure 6D:
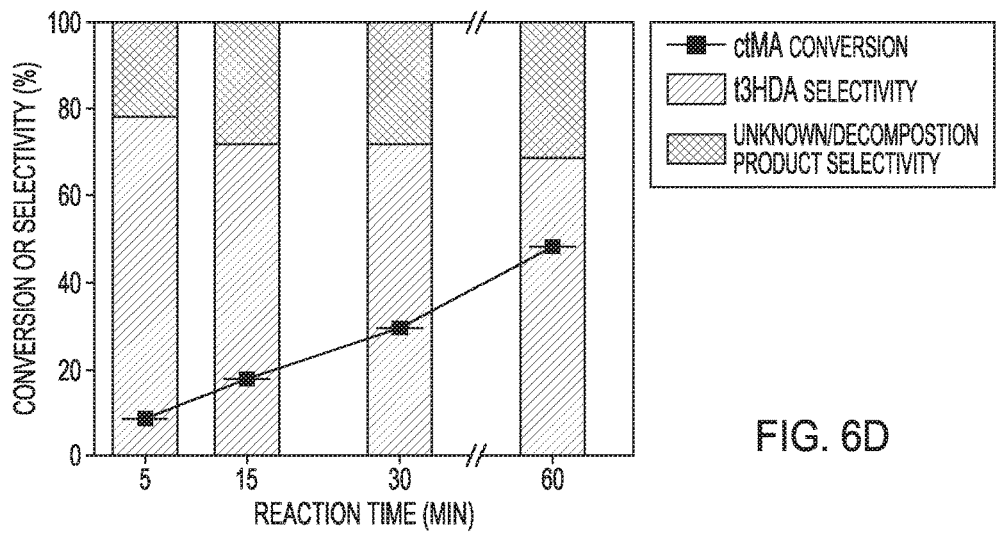
Figure 6E:
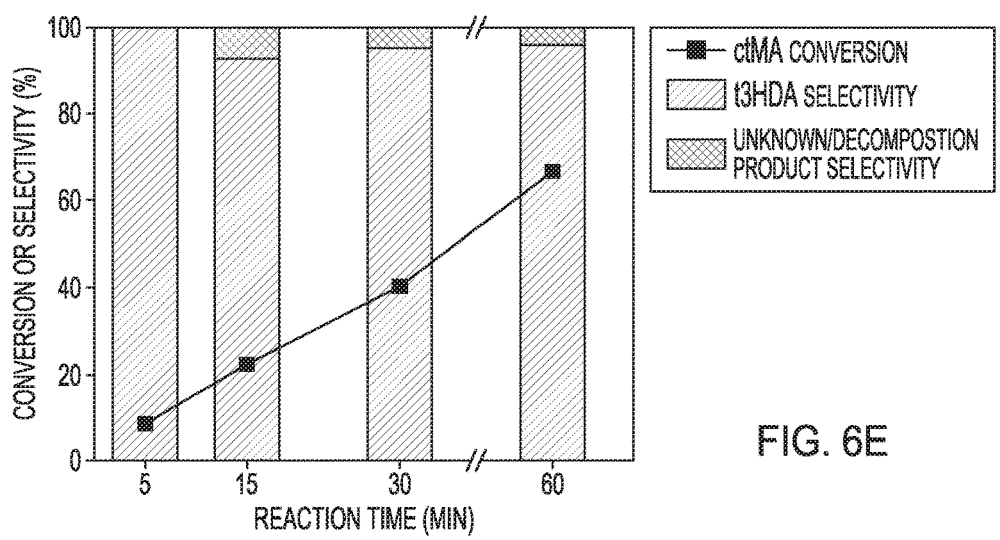
Figure 6F:
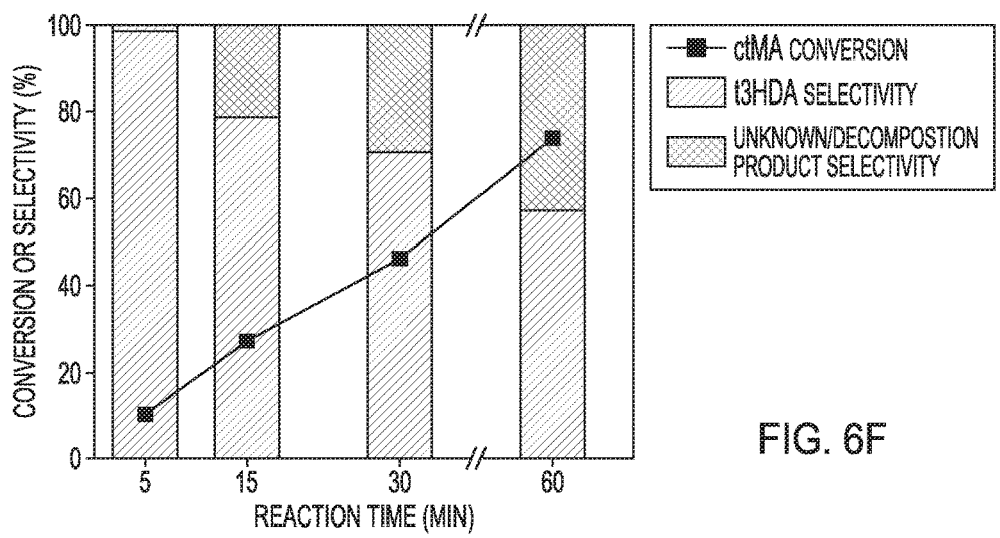
Figure 6G:
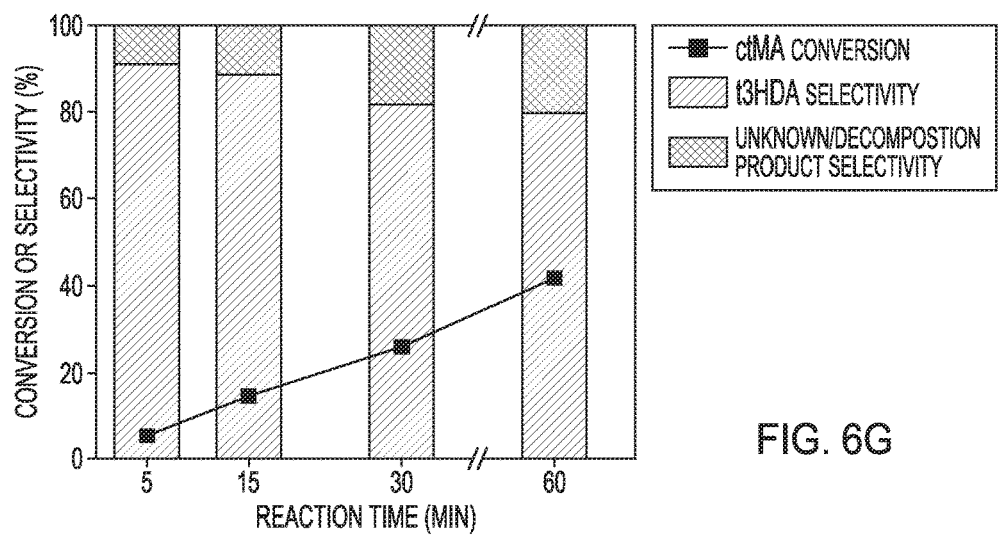
Figure 6H:
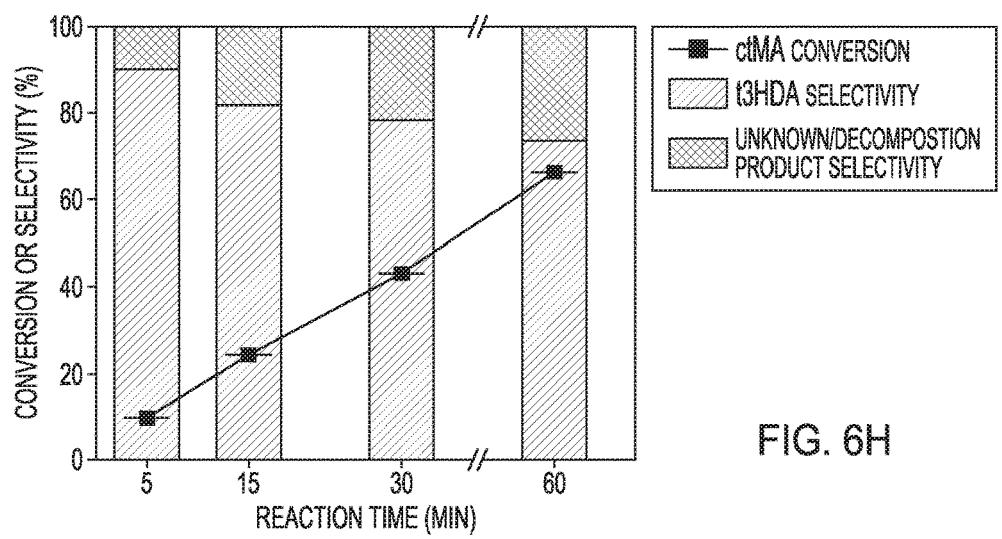
Figure 6I:
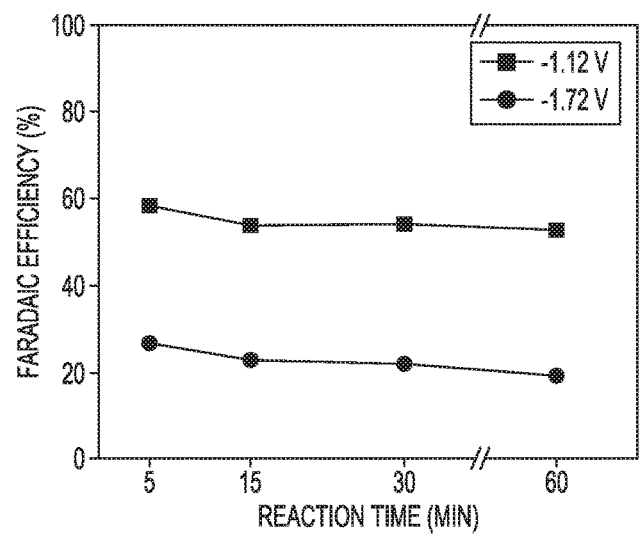
Figure 6J:
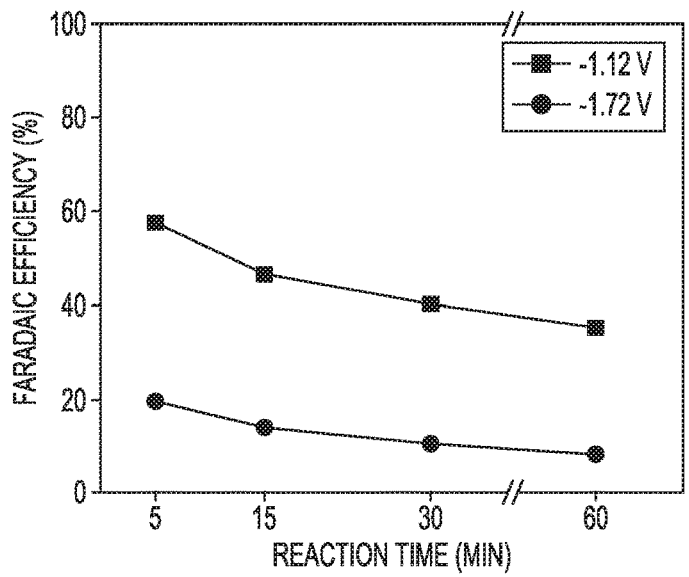
Figure 6K:
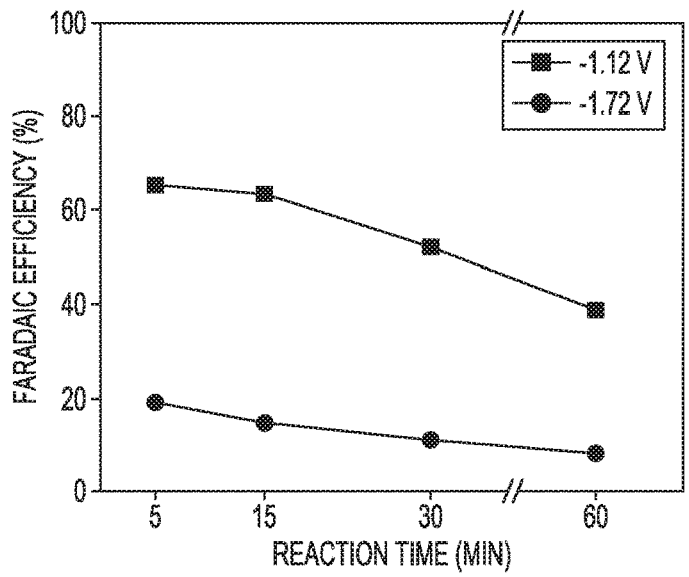
Figure 6L:
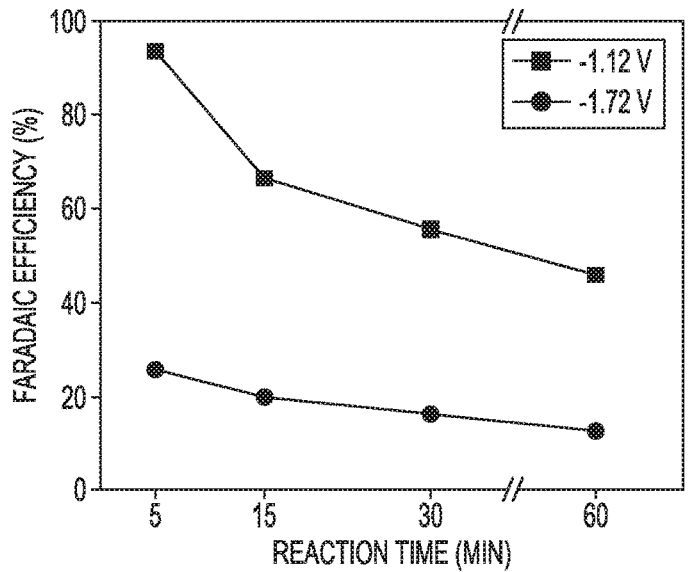

On sheet 5 of 18, Fig. 5H, delete "UNKNOWN/DECOMPOSTION" and insert --UNKNOWN/DECOMPOSITION-- therefor On sheet 5 of 18, Fig. 5I, delete "UNKNOWN/DECOMPOSTION" and insert --UNKNOWN/DECOMPOSITION-- therefor On sheet 6 of 18, Fig. 5J, delete "UNKNOWN/DECOMPOSTION" and insert --UNKNOWN/DECOMPOSITION-- therefor On sheet 8 of 18, Fig. 6A, delete "UNKNOWN/DECOMPOSTION" and insert --UNKNOWN/DECOMPOSITION-- therefor On sheet 8 of 18, Fig. 6B, delete "UNKNOWN/DECOMPOSTION" and insert --UNKNOWN/DECOMPOSITION-- therefor On sheet 8 of 18, Fig. 6C, delete "UNKNOWN/DECOMPOSTION" and insert --UNKNOWN/DECOMPOSITION-- therefor On sheet 9 of 18, Fig. 6D, delete "UNKNOWN/DECOMPOSTION" and insert --UNKNOWN/DECOMPOSITION-- therefor On sheet 9 of 18, Fig. 6E, delete "UNKNOWN/DECOMPOSTION" and insert --UNKNOWN/DECOMPOSITION-- therefor On sheet 9 of 18, Fig. 6F, delete "UNKNOWN/DECOMPOSTION" and insert --UNKNOWN/DECOMPOSITION-- therefor On sheet 10 of 18, Fig. 6G, delete "UNKNOWN/DECOMPOSTION" and insert --UNKNOWN/DECOMPOSITION-- therefor On sheet 10 of 18, Fig. 6H, delete "UNKNOWN/DECOMPOSTION" and insert --UNKNOWN/DECOMPOSITION-- therefor On sheet 12 of 18, Fig. 7A, delete "UNKNOWN/DECOMPOSTION" and insert --UNKNOWN/DECOMPOSITION-- therefor On sheet 14 of 18, Fig. 9A, delete "UNKNOWN/DECOMPOSTION" and insert --UNKNOWN/DECOMPOSITION-- therefor On sheet 15 of 18, Fig. 10B, delete "UNKNOWN/DECOMPOSTION" and insert --UNKNOWN/DECOMPOSITION-- therefor In the Specification In Column 2, Line 13, delete "Diels-Aider" and insert --Diels-Alder-- therefor

CERTIFICATE OF CORRECTION (continued)
U.S. Pat. No. 10,465,043 B2

In Column 3, Line 13, delete "an" and insert --on-- therefor

In Column 4, Line 50, delete "$CF_2$," and insert --$CF_3$,-- therefor

In Column 4, Lines 51-52, delete "$SO_1N(R)_2$," and insert --$SO_2N(R)_2$,-- therefor In Column 5, Line 12, delete "enmities;" and insert --enamines;-- therefor In Column 5, Line 15, delete "include." and insert --include-- therefor In Column 8, Line 18, delete "inuconic" and insert --muconic-- therefor In Column 8, Line 65, delete "cis, trans-muconic" and insert --cis,trans-muconic-- therefor In Column 8, Line 66, delete "cis,cis-muconic;" and insert --cis,cis-muconic-- therefor In Column 9, Line 2, delete "cis,cis-muconic;" and insert --cis,cis-muconic-- therefor In Column 10, Line 3, delete "1.00%," and insert --100%,-- therefor In Column 10, Line 30, delete "terephthalic," and insert --terephthalic-- therefor In Column 10, Line 34, delete "γ-vaierolactone" and insert --γ-valerolactone-- therefor In Column 11, Line 34, delete "Ph" and insert --Pb-- therefor In Column 11, Line 40, delete "Ph" and insert --Pb-- therefor In Column 11, Line 47, delete "her" and insert --in-- therefor In Column 11, Lines 59-60, delete "instruments" and insert --Instruments-- therefor In Column 13, Line 2, delete "Tap" and insert --$T_{BP}$-- therefor In Column 13, Line 5, after "value", insert --,--

In Column 14, Line 31, delete "reaction_" and insert --reaction-- therefor

In Column 14, Line 36, delete "ECU" and insert --ECH-- therefor

In Column 15, Line 57, delete "Bolide," and insert --Bonde,-- therefor

In Column 17, Line 10, delete "Obtained" and insert --obtained-- therefor

In Column 17, Line 38, delete "Ph" and insert --Pb-- therefor

CERTIFICATE OF CORRECTION (continued)
U.S. Pat. No. 10,465,043 B2

In Column 17, Line 66, delete "Ph" and insert --Pb-- therefor

In Column 18, Line 49, delete "(TOE)." and insert --(TOF).-- therefor

In Column 18, Line 56, delete "Ph" and insert --Pb-- therefor

In Column 18, Line 61, delete "Ph" and insert --Pb-- therefor

In Column 19, Line 13, delete "Ph" and insert --Pb-- therefor

In Column 19, Line 48, delete "Ph," and insert --Pb,-- therefor

In Column 19, Line 54, delete "r3HDA" and insert --t3HDA-- therefor

In Column 19, Line 58, delete "Observed" and insert --observed-- therefor

In Column 20, Line 15, delete "Cis, Trans-muconic" and insert --Cis,Trans-muconic-- therefor In Column 20, Line 16, delete "cis, cis-muconic" and insert --cis.cis-muconic-- therefor In Column 20, Line 46, delete "medium," and insert --medium.-- therefor In Column 21, Line 37, delete "trans, trans-muconic" and insert --trans,trans-muconic-- therefor In Column 21, Line 53, delete "hexarnethylenediamine" and insert --hexamethylenediamine-- therefor In Column 22, Line 64, delete "Pd C," and insert --Pd/C,-- therefor In Column 23, Line 27, delete "organic," and insert --organic-- therefor In Column 25, Line 13, delete "trans,trans-inuconic" and insert --trans,trans-muconic-- therefor